US009194799B2

(12) United States Patent
Baba

(10) Patent No.: US 9,194,799 B2
(45) Date of Patent: *Nov. 24, 2015

(54) IMAGING BASED REFRACTOMETERS

(71) Applicant: UT-Battelle, LLC, Oak Ridge, TN (US)

(72) Inventor: Justin S. Baba, Knoxville, TN (US)

(73) Assignee: UT-Battelle, LLC, Oak Ridge, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/103,746

(22) Filed: Dec. 11, 2013

(65) Prior Publication Data
US 2014/0104601 A1    Apr. 17, 2014

Related U.S. Application Data

(63) Continuation-in-part of application No. 13/768,802, filed on Feb. 15, 2013.

(60) Provisional application No. 61/610,094, filed on Mar. 13, 2012.

(51) Int. Cl.
*G01N 21/41* (2006.01)
*G01N 21/43* (2006.01)

(52) U.S. Cl.
CPC ............ *G01N 21/4133* (2013.01); *G01N 21/43* (2013.01)

(58) Field of Classification Search
CPC .......... G01N 21/553; G01N 2021/212; G01N 2021/215; G01N 21/43; G01N 21/4133; G01B 11/0625
USPC ................ 356/432–440, 128–137, 445–448, 356/630–632
See application file for complete search history.

(56) References Cited

U.S. PATENT DOCUMENTS

| | | | | |
|---|---|---|---|---|
| 3,449,051 A * | 6/1969 | Levitt | ............................ | 356/130 |
| 4,011,015 A * | 3/1977 | Baba | ............................ | 356/136 |
| 4,692,024 A * | 9/1987 | Bloss | ............................ | 356/135 |
| 5,822,073 A | 10/1998 | Yee et al. | | |
| 6,493,097 B1 * | 12/2002 | Ivarsson | ........................ | 356/630 |
| 7,187,444 B2 * | 3/2007 | Naya et al. | .................... | 356/445 |
| 7,233,391 B2 * | 6/2007 | Schermer et al. | ............. | 356/246 |

(Continued)

OTHER PUBLICATIONS

Baba et al., "Full-Field Imaging-Based Instantaneous Hyperspectral Absolute Refractive Index Measurement," Opt. Lett. 37(9), 1520-1522 (2012).

(Continued)

*Primary Examiner* — Hoa Pham
(74) *Attorney, Agent, or Firm* — Klarquist Sparkman, LLP

(57) ABSTRACT

Refractometers for simultaneously measuring refractive index of a sample over a range or wavelengths of light include dispersive and focusing optical systems. An optical beam including the rang of wavelengths is spectrally spread along a first axis and focused along a second axis so as to be incident to an interface between the sample and a prism at a range of angles of incidence including a critical angle for at least one wavelength. In some cases, the prism can have a triangle, parallelogram, trapezoid, or other shape. In some cases, the optical beam can be reflected off of multiple interfaces between the prism and the sample. An imaging detector is situated to receive the spectrally spread and focused light from the interface and form an image corresponding to angle of incidence as a function of wavelength. One or more critical angles are indentified and corresponding refractive indices are determined.

21 Claims, 11 Drawing Sheets

(56) References Cited

U.S. PATENT DOCUMENTS

| | | | |
|---|---|---|---|
| 7,619,725 B1* | 11/2009 | Seaver | 356/137 |
| 7,755,763 B2* | 7/2010 | Anders et al. | 356/436 |
| 7,879,619 B2* | 2/2011 | Jing et al. | 436/171 |
| 2002/0126290 A1* | 9/2002 | Naya | 356/445 |
| 2003/0169417 A1* | 9/2003 | Atkinson et al. | 356/135 |
| 2004/0145731 A1* | 7/2004 | Nakajima et al. | 356/135 |
| 2007/0279635 A1* | 12/2007 | Wu et al. | G01N 21/553 356/445 |
| 2011/0194109 A1* | 8/2011 | kahre | 356/326 |
| 2013/0242115 A1 | 9/2013 | Baba et al. | |
| 2013/0293875 A1 | 11/2013 | Wagner | |

OTHER PUBLICATIONS

Boudreaux, Spectroscopy Using Short-Path Surface Plasmon Dispersion, Master of Science Thesis, University of Tennessee, Knoxville (2004).

Castrejón-Pita et al., "Critical Angle Laser Refractometer," Rev. Sci. Instrum. 77, 035101-1 to -4 (2006).

Ferrell et al., "Plasmons and Surfaces," American Scientist 73(4), 344-353 (1985).

Guo et al., "A Two-Reflection Divergent Differentiating Critical Angle Refractometer," Rev. Sci. Instrum. 82, 053108, 9pp. (May 27, 2011).

Guo et al., "A Local Curve-Fitting Method for the Complex Refractive Index Measurement of Turbid Media," Meas. Sci. Technol. 23, 047001, 5pp. (Mar. 7, 2012).

Kim et al., "Absolute Refractive Index Measurement Method Over a Broad Wavelength Region Based on White-Light Interferometry," Appl. Opt. 49(5), 910-914 (2010).

Pixton et al., "Automated Measurement of the Refractive Index of Fluids," Appl. Opt. 47(10), 1504-1509 (2008).

\* cited by examiner

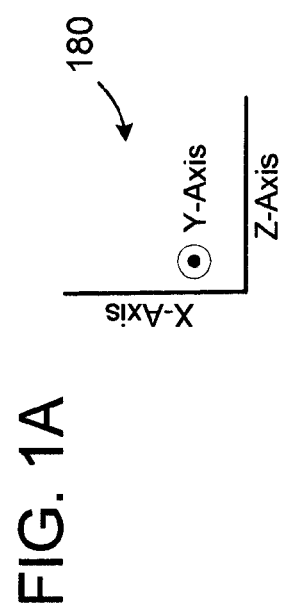
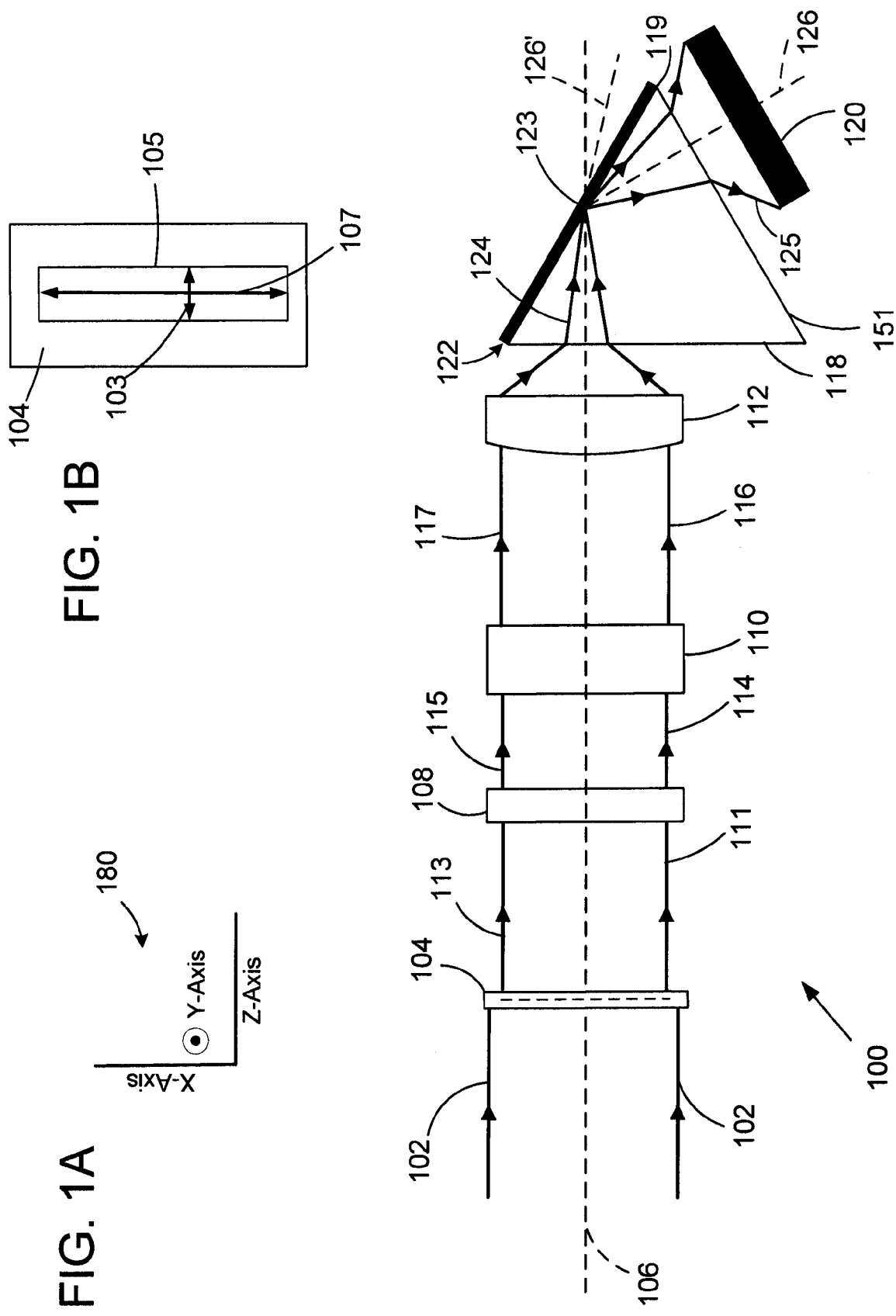
FIG. 1A
FIG. 1B

IMAGING BASED REFRACTOMETERS

CROSS REFERENCE TO RELATED APPLICATIONS

This application is a continuation-in-part of U.S. application Ser. No. 13/768,802, filed Feb. 15, 2013, which claims the benefit of U.S. Provisional Application No. 61/610,094, filed Mar. 13, 2012, both of which applications are hereby incorporated herein by reference in their entirety.

ACKNOWLEDGMENT OF GOVERNMENT SUPPORT

This invention was made with government support under Contract No. DE-AC05-000R22725 awarded by the U.S. Department of Energy. The government has certain rights in the invention.

FIELD

This disclosure pertains to methods and apparatus for measuring refractive index.

BACKGROUND

The refractive index (RI) of a material—that is, the ratio of the speed of light in a vacuum to the speed of light in the material—can be an important property for use in species identification and material characterization. For example, in industries such as food production and pharmaceuticals, RI can be used as a measure of product quality or to characterize reactions and other dynamic processes. More specifically, precise species identification can be achieved using multi-wavelength RI measurement, and the ability to perform real-time or continuous multi-wavelength RI measurements can be useful for monitoring the properties of analytes and other chemical constituents. Conventional refractometers and techniques for measuring RI have various drawbacks and limitations. Thus, new techniques for RI measurements are still needed.

SUMMARY

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

Refractometers comprise a focusing optical system configured to direct an optical beam that includes a range of wavelengths to be incident on an interface between the sample and a prism at a range of angles of incidence including a critical angle, and a dispersive optical system configured to spectrally spread the optical beam so that the range of wavelengths and the critical angle are independently detectable. In some examples, the dispersive optical system comprises a diffraction grating configured to spectrally spread the optical beam by imposing a wavelength dependent angular dispersion along a first axis and a cylindrical lens configured to collimate the spectrally spread optical beam along the first axis to produce a collimated spectrally spread optical beam. In representative embodiments, refractometers comprise a detector configured to receive the spectrally spread optical beam and to generate one or more two-dimensional images having pixel coordinates associated with the range of wavelengths and the range of angles of incidence. The prism can be an equilateral sapphire or SF10 optical glass prism. However, the prism shape and materials are not so limited, and the prism can have a variety of suitable shapes and comprise a variety of suitable materials. In some implementations, refractometers comprise a light source configured to produce the optical beam and so that the optical beam is substantially collimated and a slit is oriented so that a longer dimension is substantially perpendicular to the first axis and configured to reduce spectral overlap in the spectrally spread optical beam.

In some examples, the focusing optical system comprises a cylindrical lens configured to focus the collimated spectrally spread optical beam along a second axis substantially perpendicular to the first axis so as to establish the range of angles of incidence. In other examples, the focusing optical system comprises a second cylindrical lens situated upstream from the dispersive optical system and configured to focus the optical beam along a second axis substantially perpendicular to the first axis so as to establish the range of angles of incidence. In further examples, refractometers comprise a collimating optical system configured to receive the optical beam from the interface between the sample and the prism and to direct a substantially collimated optical beam to the diffraction grating.

Refractometers comprise a dispersive optical system configured to receive a collimated optical beam and to spectrally disperse a range of wavelengths of the optical beam along a first axis. A first cylindrical lens is configured to collimate the spectrally dispersed optical beam along the first axis, and a second cylindrical lens is configured to converge the collimated spectrally dispersed light along a second axis that is not parallel to the first axis. A prism having a surface configured to contact a sample is situated to receive the converged optical beam at an interface between the surface and the sample. A detection system is situated and configured to detect critical angles of the sample for at least two wavelengths of the range of wavelengths. The second cylindrical lens and the prism can be configured to produce critical angle total internal reflection at the interface over at least a portion of the range of wavelengths. The prism can have any of various suitable shapes, and in one example can be an equilateral prism. In some examples, the dispersive optical system comprises a diffraction grating having grooves oriented parallel to the second axis.

In some implementations, refractometers comprise a slit with a longer dimension oriented parallel to the second axis and configured to reduce spectral overlap of the spectrally dispersed optical beam produced by the dispersive optical system, wherein the slit is situated at an angle relative to the diffraction grating so that a first order of diffracted light is collected by the first cylindrical lens. In representative examples, refractometers include a sample holder configured to maintain the contact between the surface of the prism and the sample and including a channel to enable flow-through of the sample. The sample can be a gas, a liquid or a liquid-gel. In some examples, refractometers comprise a light source configured to produce the collimated optical beam.

Methods of measuring refractive index of a sample at a plurality of wavelengths comprise directing an optical beam that includes optical radiation at the plurality of wavelengths so as to be incident on an interface between the sample and a prism at a plurality of angles of incidence and spectrally spreading the optical beam to determine if the plurality of angles of incidence includes a critical angle for one or more of the plurality of wavelengths. In some examples, the methods further comprise identifying a critical angle for at least one of the plurality of wavelengths and/or determining a refractive index of the sample at at least one of the plurality of wavelengths. In representative embodiments, the methods comprise generating at least one two-dimensional image having a first axis corresponding to at least a portion of the plurality of wavelengths and a second axis corresponding to at least a portion of the plurality of angles of incidence. In further examples, the methods comprise determining refractive index of the sample as a function of wavelength from the at least one two-dimensional image.

In some implementations, the spectrally spreading of the optical beam comprises imposing a wavelength dependent angular dispersion on the optical beam along a first axis and collimating the angularly dispersed optical beam to produce a collimated spectrally dispersed optical beam. In further implementations, the directing of the optical beam comprises focusing the collimated spectrally dispersed optical beam along a second axis that is not parallel to the first axis so as to generate the range of angles of incidence. In some examples, the first axis is perpendicular to the second axis.

Methods of refractive index measurement comprise, identifying critical pixel locations from one or more images, and estimating refractive index for the test sample at at least two wavelengths of the plurality of wavelengths using a refractive-index-calibration relationship and the identified critical pixel locations. In some examples, the methods comprise deriving a wavelength-calibration relationship expressing wavelength as a function of one or more pixel coordinates using a set of wavelength calibration images collected with one or more light sources having known emission spectra, wherein the estimating of the refractive index is based on the wavelength-calibration relationship. In other examples, the methods comprise deriving the refractive-index-calibration relationship using a set of refractive index calibration images collected using one or more calibration samples having known refractive index dispersion profiles, wherein the refractive-index-calibration relationship expresses measured refractive index as a function of critical pixel location.

In some implementations, refractometers for multi-wavelength measurement of refractive index of a sample are configured so that at least portions of an optical beam are totally internally reflected within a prism at a first reflection area and at least portions of the optical beam are totally internally reflected within the prism at a second reflection area. In some cases, the prism comprises a first surface and a second surface parallel to the first surface, wherein the first surface and the second surface are situated so as to contact the sample and the first surface includes the first reflection area and the second surface includes the second reflection area.

In some specific implementations, the optical beam is directed to the first surface and the second surface at a range of angles of incidence that includes the critical angle. In some cases, the optical beam is directed so as to be incident to the first surface at least twice. In some cases, the prism further comprises a reflective surface configured to direct the optical beam from the first surface to the second surface. In some cases, such a reflective surface is perpendicular to the first surface and the second surface. In some cases, a cross-section of the prism is a parallelogram. In some cases, a cross-section of the prism is a trapezoid.

In some specific implementations, a prism comprises a first subprism having a first surface including the first reflection area, and a second subprism having a second surface including the second reflection area, and the optical beam is directed to the first surface and the second surface at a range of angles of incidence that includes the critical angle. In some cases, one of the first subprism and the second subprism has a triangular cross-section. In some cases, the first surface is parallel to the second surface and the first subprism is not in contact with the second subprism.

In some specific implementations, a cross-section of a prism is a quadrilateral, the prism has a first surface in contact with the sample and a second surface in contact with the sample, the refractometer further comprises a reflective material in contact with a third surface of the prism, and the refractometer is configured to reflect the optical beam at a third reflection area and to at least partially reflect the optical beam within the prism at a fourth reflection area. In some cases, the first reflection area is at an interface between the first surface of the prism and the sample, the second reflection area is at an interface between the second surface of the prism and the sample, the third reflection area is at an interface between the third surface of the prism and the reflective material, and the fourth reflection area is at an interface between the first surface of the prism and the sample.

In some implementations, a refractometer comprises a spectrally and angularly dispersive optical system configured to receive a collimated optical beam and to spectrally disperse a range of wavelengths of the optical beam along a first axis and angularly disperse the optical beam along a second axis that is not parallel to the first axis, a prism in contact with a sample, wherein the prism is configured so that at least a portion of an incident optical beam is reflected within the prism at an interface between the sample and a prism surface at a first reflection area and at a second reflection area, and a detection system situated and configured to detect critical angles of the sample for at least two wavelengths of the range of wavelengths based on the partial reflections of the optical beam at the first and second reflection areas.

In some specific implementations, such a refractometer further comprises a first cylindrical lens configured to collimate the spectrally dispersed optical beam along the first axis and a second cylindrical lens configured to angularly disperse the collimated spectrally dispersed optical beam along a second axis that is not parallel to the first axis.

In some implementations, a method of measuring refractive index of a sample at a plurality of wavelengths, comprises directing an optical beam that includes optical radiation at the plurality of wavelengths so as to be incident on an interface between the sample and a prism at a plurality of angles of incidence, thereby causing at least partial reflection of the optical beam within the prism at a first reflection area and at least partial reflection of the optical beam within the prism at a second reflection area, and spectrally spreading the optical beam to determine if the plurality of angles of incidence includes a critical angle for one or more of the plurality of wavelengths.

The foregoing and other features and advantages will become more apparent from the following detailed description, which proceeds with reference to the accompanying figures.

BRIEF DESCRIPTION OF THE DRAWINGS

FIG. 1A is a side view of a representative critical angle refractometer.

FIG. 1B is a front view an aperture plate defining a slit.

DETAILED DESCRIPTION

Figure 2:
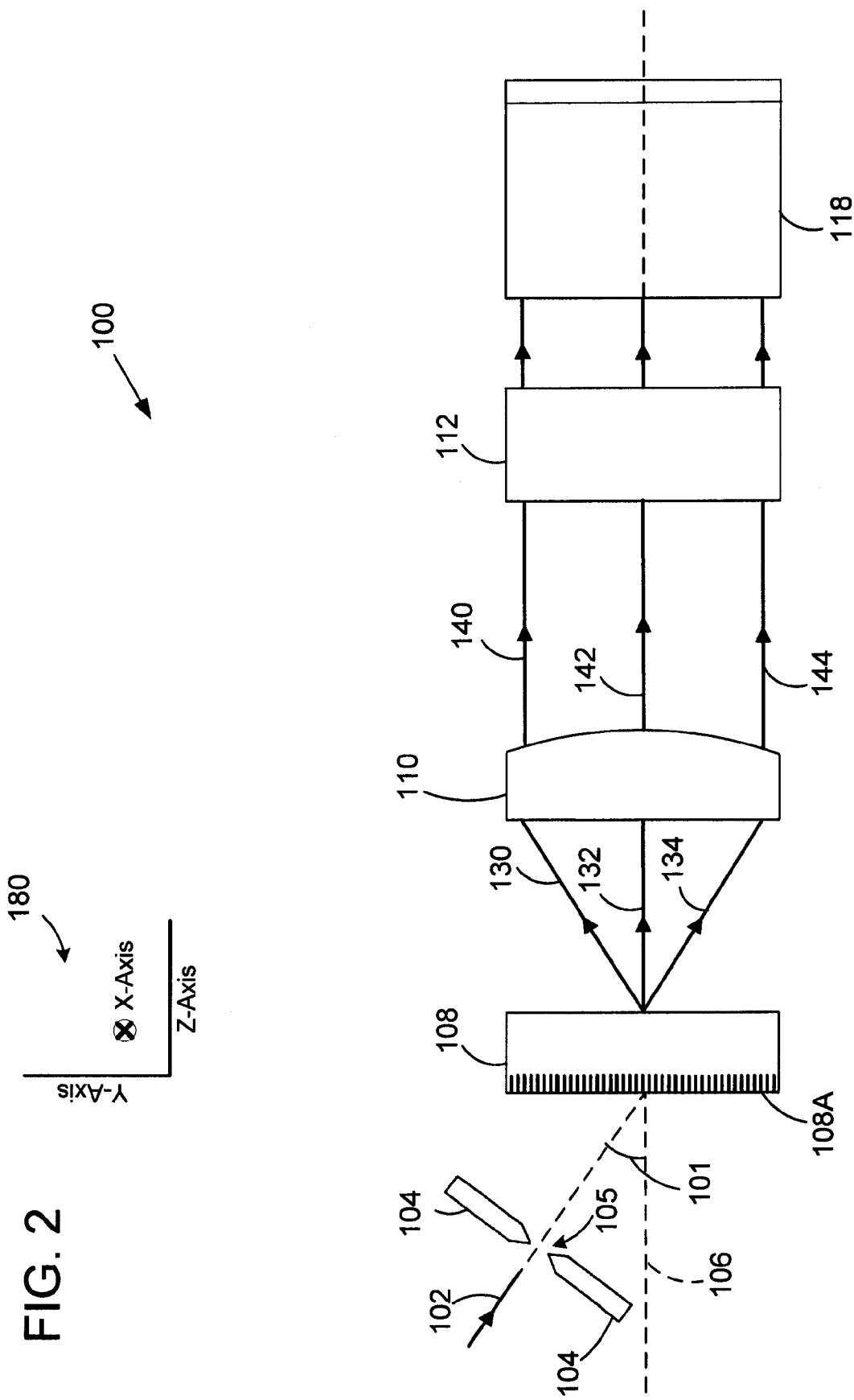
FIG. 2 is a top view of the refractometer of FIG. 1A.

The following disclosure is presented in the context of representative embodiments that are not to be construed as being limiting in any way. This disclosure is directed toward all novel and non-obvious features and aspects of the various disclosed embodiments, alone and in various combinations and sub-combinations with one another. The disclosed methods, apparatus, and systems are not limited to any specific aspect or feature or combination thereof, nor do the disclosed embodiments require that any one or more specific advantages be present or problems be solved.

Although the operations of the disclosed methods are described in a particular, sequential order for convenient presentation, it should be understood that this manner of description encompasses rearrangement of the operations, unless a particular ordering is required by specific language set forth below. For example, operations described sequentially may in some cases be rearranged or performed concurrently. Moreover, for the sake of simplicity, the attached figures may not show the various ways in which the disclosed systems, methods, and apparatus can be used in conjunction with other things and methods.

This disclosure sometimes uses terms like "produce," "generate," "select," "receive," "exhibit," and "provide" to describe the disclosed methods. These terms are high-level abstractions of the actual operations that are performed. The actual operations that correspond to these terms may vary depending on the particular implementation and are readily discernible by one of ordinary skill in the art.

The singular forms "a," "an," and "the" include the plural forms unless the context clearly dictates otherwise. The term "includes" means "comprises." Unless the context dictates otherwise, the term "coupled" means mechanically, electrically, or electromagnetically connected or linked and includes both direct connections or direct links and indirect connections or indirect links through one or more intermediate elements not affecting the intended operation of the described system.

Certain terms may be used such as "top," "side," "front," "back," and the like. These terms are used, where applicable, to provide some clarity of description when dealing with relative relationships. But, these terms are not intended to imply absolute relationships, positions, and/or orientations.

The term "or" refers to a single element of stated alternative elements or a combination of two or more elements, unless the context clearly indicates otherwise.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting. Other features of the disclosure are apparent from the following detailed description and the claims.

Unless otherwise indicated, all numbers expressing quantities of components, percentages, temperatures, times, and so forth, as used in the specification or claims are to be understood as being modified by the term "about" or "approximately." Accordingly, unless otherwise indicated, implicitly or explicitly, the numerical parameters set forth are approximations that may depend on the desired properties sought and/or limits of detection under standard test conditions/methods. When directly and explicitly distinguishing embodiments from discussed prior art, the embodiment numbers are not approximates unless the word "about" is recited.

Refractometers described herein use critical angle total internal reflection to determine the refractive index (RI) of a sample. The critical angle is the angle at which light incident on an interface between two media having different RIs (e.g., $n_1$ and $n_2$) transitions from partial transmission to complete reflection (total internal reflection (TIR)). TIR occurs at the critical angle and at angles of incidence greater than the critical angle. According to Snell's law, the critical angle $\theta_c$ is defined as follows:

$$\theta_c = \sin^{-1}(n_2/n_1), \text{ where } n_1 > n_2.$$

Because the RI of a material is typically a function of wavelength, critical angle also varies as a function of wavelength.

In examples of the disclosed critical angle refractometers, a sample is placed in contact with a surface of a prism with a known RI. The critical angle is measured by directing light to the prism surface in contact with the sample and detecting light reflected at the prism-sample interface. The reflected light can be detected using an imaging detector such as a charge-coupled device (CCD) or other imaging device suitable for detecting the wavelengths associated with the light. The imaging detector is configured to produce an image that can be displayed or stored. The produced images include a transition region in which pixel intensities transition from dark to light (e.g., detected light intensity transitions from relatively low intensity to relatively high intensity). This indicates the transition from partial transmission to TIR that occurs at the critical angle and at angles of incidence greater than the critical angle. Image pixel(s) corresponding to this transition region can be referred to as critical pixel(s) $P_c$.

The critical angle can be determined based on critical pixel location in the image. The index of refraction is then calculated from the critical angle using Snell's law as discussed above. For a critical angle refractometer, $n_1$ is the index of refraction of the prism, and $n_2$ is the index of refraction of the sample. Because the index of refraction of the prism is known, the RI of the sample is determined by measuring the critical angle $\theta_c$.

FIGS. 1-4 illustrate representative critical angle refractometers that enable multi-wavelength measurement of RI of a sample. That is, RI can be measured for a range of wavelengths either sequentially or simultaneously. As used herein, a range of wavelengths includes a plurality of wavelengths and can be a continuous or non-continuous plurality of wavelengths. The refractometers described herein can provide for hyperspectral measurement of RI.

FIG. 1A is a side view of a representative refractometer 100, and FIG. 2 is a top view of the refractometer of FIG. 1A. In the following discussion, references to an xyz-coordinate system 180 are made to facilitate convenient description of the refractometer 100. As shown in FIG. 1A, a y-axis extends outwardly from the plane of FIG. 1A. As shown in FIG. 2, the x-axis extends into the plane of FIG. 2. The coordinate system 180 is provided only to simplify the description, and the refractometer 100 is not limited to particular arrangement in any coordinate system.

Referring to FIGS. 1A and 2, a collimated optical beam 102 is directed to an aperture plate 104 that defines a slit 105, which produces an optical beam 111, 113. FIG. 1B is a front enlarged view of the aperture plate 104 and illustrates the dimensions of the slit 105. As shown in FIG. 1B, the slit 105 has a shorter dimension 103 (width W) and a longer dimension 107 (length L) perpendicular to the shorter dimension in a plane defined by the aperture plate 104. The aperture plate 104 is situated within the refractometer 100 so that the longer dimension 107 is parallel to the x-axis.

The optical beam 102 is substantially collimated at least along the width W of the slit 105 (i.e., in the yz-plane). The optical beam 102 can be multi-wavelength light (e.g., generated by a broadband white light source, an infrared source, etc.), or the optical beam 102 can be monochromatic (e.g., generated by a discrete wavelength source or using filters). The light source (not shown) for the optical beam 102 produces optical radiation in a range or spectrum of wavelengths over which an RI measurement is to be made. For example, to measure the RI of a sample for wavelengths between 400 nm and 700 nm, the source for the optical beam 102 includes at least wavelengths ranging from 400 nm to 700 nm. In some examples, multiple sources are used.

In general, dimensions of the slit 105 are selected in association with the angular spread of the optical beam 102 and to minimize or reduce spectral overlaps. Typically, the optical beam 102 is substantially collimated and the slit width W is selected so as to reduce or eliminate spectral overlap in the diffracted optical beam produced by the diffraction grating 108. For example, the slit 105 can reduce the angular spread of a transmitted optical beam in the yz-plane, as shown by ray lines 111, 113, to improve collimation of the optical beam 102. Wide slits are associated with greater spectral overlap and reduced spectral resolution, but do permit higher power in the diffracted optical beam.

Because the slit 105 can reduce the intensity of the optical beam entering the refractometer thereby reducing signal-to-noise ratio, it is generally preferred to select a relatively large slit width W. For example, the slit width W can be 10, 100, 200, 500 or 1000 times a central wavelength or other wavelength associated with the optical beam 102. The slit length L is typically much larger than the width W and is selected based on the preferred size of the transmitted optical beam in the xz-plane. For example, the length L can be approximately the same size or greater than the aperture of cylindrical lenses 110 or 112 in the xz-plane. In some implementations, the slit 105 may not be needed. For example, spectral resolution of the refractometer 100 may be sufficient without use of the slit 105.

Referring to FIG. 1, the transmitted optical beam is received along the ray lines 111, 113 by a diffraction grating 108. The grating 108 is situated so as to produce a spectrally dispersed beam 114, 115. Referring to FIG. 2, a groove layer 108A of the grating 108 includes grooves oriented parallel to the x-axis and parallel to the longer dimension 107 of the slit 105. The grating 108 diffracts the optical beam transmitted by the slit 105 within the yz-plane, as illustrated by ray lines 130, 132, 134. The transmitted optical beam is spectrally spread by the grating 108 to form a spectrally dispersed optical beam that propagates as shown by ray lines 114, 115 and with wavelength varying in the yz-plane as a function of distance from (or angle of propagation relative to) an optical axis 106.

Although the grating 108 is illustrated as a transmissive grating, the refractometer 100 can be modified to instead include a reflective grating. In general, spectral resolution of the refractometer depends at least in part on the dispersive effect of the grating 108. Thus, the grating 108 is preferably configured to produce a large dispersion. That is, the grating 108 can be configured to produce a large angular or spatial dispersion or spreading of incident wavelengths (i.e., spectral dispersion). Since such angular spread or separation of wavelengths increases as groove or slit separation decreases, the grating can have a groove or slit spacing that is on the order of the wavelength being measured. For example, groove spacing can be less than about 1.5, 2, 3, 4 or 5 times a central wavelength or other wavelength associated with the optical beam 102. The grating 108 can be an enhanced resolution transmission grating, a blazed grating, a holographic grating, or other spectrally dispersive element. Additionally, any other dispersive optical components configured to separate spectral components of an optical beam such as prisms can be used.

As shown in FIG. 2, the optical beam 102 can be oriented at an angle 101 relative to the optical axis 106. The angle 101 can be selected so that a selected range of wavelengths at which critical angle is to be measured is approximately centered on the optical axis 106. For example, ray lines 130, 134 represent directions of propagation of maximum and minimum wavelengths within the selected wavelength range. Ray line 132 represents a direction of propagation of a central wavelength within the selected wavelength range. Ray lines 130, 132, 134 are typically associated with a first diffraction order produced by the grating 108, but other diffraction orders can be used.

The spectrally dispersed beam 114, 115 produced by the diffraction grating 108 is received by a first cylindrical lens 110 to produce a collimated, spectrally dispersed beam as indicated by ray lines 116, 117, 140, 144. The cylindrical lens 110 is positioned and oriented so as to collimate the spectrally dispersed beam in the direction of the diffraction produced by the grating 108. That is, the cylindrical lens 110 collimates the spectrally spread beam in the yz-plane, and the optical beam produced by the cylindrical lens 110 is also spectrally separated. For example, as shown in FIG. 2, the cylindrical lens 110 redirects the light propagating according to the ray line 130 along a ray line 140, the light propagating according to the ray line 132 along a ray line 142, and the light propagating according to the ray line 134 along a ray line 144. As shown, the ray lines 140, 142, 144 are substantially parallel to but spatially separated from each other at the output of the cylindrical lens 110. As shown in FIG. 1A by the ray lines 116, 117, the optical beam produced by the cylindrical lens 110 is unchanged in the xz-plane and remains collimated in the xz-plane. Typically, the grating 108 and the cylindrical lens 110 are separated by a focal length of the cylindrical lens 110 so that the spectrally dispersed beam 114, 115 is collimated in the yz-plane.

An aperture of the cylindrical lens 110 can be selected so as to sufficiently collect diffracted light associated with the selected wavelength range. For example, the size and focal length of the cylindrical lens 110 can be selected so that, based on the divergence angles of the ray lines 130, 134 and the separation of the grating 108 and the cylindrical lens 110, the selected wavelength range is collected by the cylindrical lens 110 and has sufficient spatial separation. For example, it may be desirable to have the spatial separation of the wavelengths correspond to dimensions of a detector 120 so as to fill an active area of the detector 120. In some implementations, spectral dispersion can be increased by increasing the focal length of the cylindrical lens 110 and/or by increasing the spatial separation of the wavelengths independent of the angular spread of the wavelengths introduced by the grating 108.

The cylindrical lens 110 directs the collimated, spectrally dispersed beam 116, 117 to a second cylindrical lens 112, which is configured so as to focus the received light on or near an interface 119 between a prism 118 and a sample 123. The sample 123 is held in contact with the prism 118 using a sample holder 122.

The cylindrical lenses 110 and 112, as well as other lenses and optical components described herein, can be achromatic and/or include anti-reflection coatings. For example, the cylindrical lens 112 and/or the cylindrical lens 110 can be made from materials with low chromatic aberration for the range of wavelengths being measured. Quartz optics, which can have reduced RI dispersion in the visible wavelengths when compared to other materials such as BK7 or other optical glasses, may be used.

The optical beam produced by the cylindrical lens 112 at the interface 119 is spectrally dispersed along the y-axis and has a range of angles of incidence in the xz-plane. That is, the cylindrical lens 112 produces a focal line at the prism-sample interface 119, and the cylindrical lens 112 is oriented so that the focal line is parallel to the y-axis. Focusing the light at the prism-sample interface 119 ensures that the light is incident on the interface 119 between the prism 118 and the sample 123 at a range of angles. The angles of incidence are measured relative to a line perpendicular to the prism-sample interface. In order to increase the range of angles of incidence, the focal length of the cylindrical lens 112 can be decreased. Preferably, the range of angles of incidence includes the critical angle of the interface 119. For the critical angle and angles greater than the critical angle, light incident on the interface 119 between the prism 118 and the sample 123 is totally internally reflected and directed along an axis 126. For angles less than the critical angle, light is refracted and transmitted along an axis 126' and can be partially reflected along axis 126.

The sample 123 can take various forms (i.e., liquid, gas, liquid-gel, etc.) and can be made to contact the surface of the prism 118 using various techniques. For example, the sample 123 can be a liquid placed directly on the surface of the prism 118. A slide can be placed on the sample 123 to facilitate contact with the prism surface. In other examples, a sample holder 122 is used. In one example, the sample holder 122 includes a glass or plastic substrate (e.g., a polymer such as acetal or other similar material) housing a channel configured to retain the sample 123. The sample holder 122 is then configured to be secured to the prism 118 so that the sample 123, while in the channel, is in contact with the prism 118. The sample holder 122 can be black in color in order to reduce light reflection (e.g., from a sample holder-air interface). The sample holder 122 can be configured to allow flow-through of liquid or gaseous samples. In some examples, the channel is connected to a sample source so that a sample under investigation can be continually flowed through the channel as RI measurements are made.

The light produced by the cylindrical lens 112 is refracted, as shown by ray line 124, upon entering the prism 118. Light reflected off of the prism-sample interface is directed to and received by a detector 120, such as a CCD sensor or other sensor capable of detecting the selected wavelength range.

The detector 120 can be a full-field sensor, capable of generating a two-dimensional image from the detected light intensity. Images can be stored or displayed. Images can be collected over a predetermined period of time and/or averaged to reduce signal-to-noise ratio. For example, the images can be time integrated. The RI of the sample can be estimated from the images, as described in more detail below.

The detector 120 is positioned on the axis 126 so as to receive the light reflected from the prism-sample interface 119. The position of the detector 120 along the axis 126 relative to the prism 118 can be determined based on the active area of the detector and the desired angular resolution. In some implementations, the refractometer 100 may be configured so that the position of the detector 120 is adjustable.

In general, the resolution of the refractometer 100 can be increased when the detector 120 has a large active area, e.g., when the detector 120 is a large CCD array. However, the refractometer may be less efficient when the active area is larger than the dimensions of the collected light 125. The minimum desired active area is based on several factors, such as the RI of the prism 118, the size of the cylindrical lens 110, the cylindrical lens 112 and the prism 118, as well as the focal length of the cylindrical lens 112 and the distance between the detector 120 and the prism 118. For example, if the detector 120 is positioned at a distance from the prism 118 so as to receive light 125 when the light 125 has expanded to approximately the same size as light at the output of cylindrical lens 112, the refractometer 100 may be most efficient if the active area of the detector 120 is approximately the same size as the light at the output of the cylindrical lens 112 (i.e., the light represented by ray lines 140 and 144 in the yz-plane and by ray lines 116 and 117 in the xz-plane). In this manner, the detector 120 is positioned to detect the entire range of angles of incidence at the prism-sample interface, and the active area of the detector 120 is completely filled.

The detector 120 can be positioned closer to the prism (i.e., by decreasing the distance between the detector 120 and the prism 118 along the axis 126). However, the detector 120 will detect a range of angles of incidence with less beam spread at the detector and potentially less angular resolution. The detector can also be positioned further from the prism (i.e., by increasing the distance between the detector 120 and the prism 118 along the axis 126). In this case, the entire range of angles of incidence may not be collected unless the active area of the detector 120 is increased. However, angular resolution is increased. Angular resolution can also be increased by reducing the focal length of the cylindrical lens 112 or otherwise increasing the numerical aperture of the focused line.

Although the detector 120 is illustrated as receiving light reflected at the interface 119 of the prism 118 and the sample 123, the refractometer 100 can be re-configured so that the detector 120 receives transmitted light. For example, the detector 120 can be positioned along the side of the prism 118 with the sample 123 and positioned in the path of refracted, transmitted light along the axis 126'.

Although the prism 118 is illustrated as a single equilateral prism, other types of prisms or multiple prisms can be used. For example, a right angle prism such as a 30-60-90 prism can be used. Various other suitable prism configurations can be used, such as those described in further detail below. However, the location of the detector 120 should be adjusted accordingly based on the shape of the prism(s) and standard ray tracing techniques so that the detector 120 continues to receive the light reflected/transmitted from the prism-sample interface(s). It may be desirable to select a prism shape so as to avoid TIR of the light at the prism-air interface surface 151 that receives light reflected off the prism-sample interface 119. Entrance and exit surfaces at the prism 118 can be coated or uncoated. In some examples, the prism is a glass block or slab or a dielectric substrate that does not have a triangular-shaped geometry.

The refractive index of the prism 118 is selected based on the anticipated refractive index of the sample 123. Specifically, in order for total internal reflection to occur at the interface 119 between the sample 123 and the prism 118, the RI of the prism 118 must be higher than the RI of the sample 123. Because the RI of the prism 118 theoretically defines the maximum RI that can be measured by the refractometer 100, it is generally preferred to select a prism 118 with a high RI. For example, the prism 118 can be made of SF10 optical glass or sapphire when the range of wavelengths being measured is part of the visible spectrum. The prism 118 can be made of silicon or germanium when RI measurements are made using infrared wavelength sources. However, other materials can also be used. In addition, choosing a prism 118 with a high RI can improve wavelength resolution for long wavelengths where dispersion effects of the prism compromise TIR resolvability.

Figure 3B:
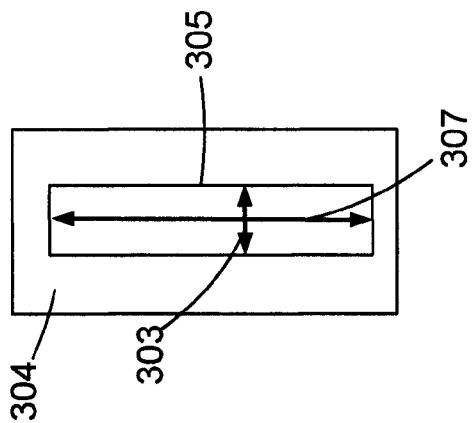
FIG. 3B is a front view of an aperture plate defining a slit.
Figure 3A:
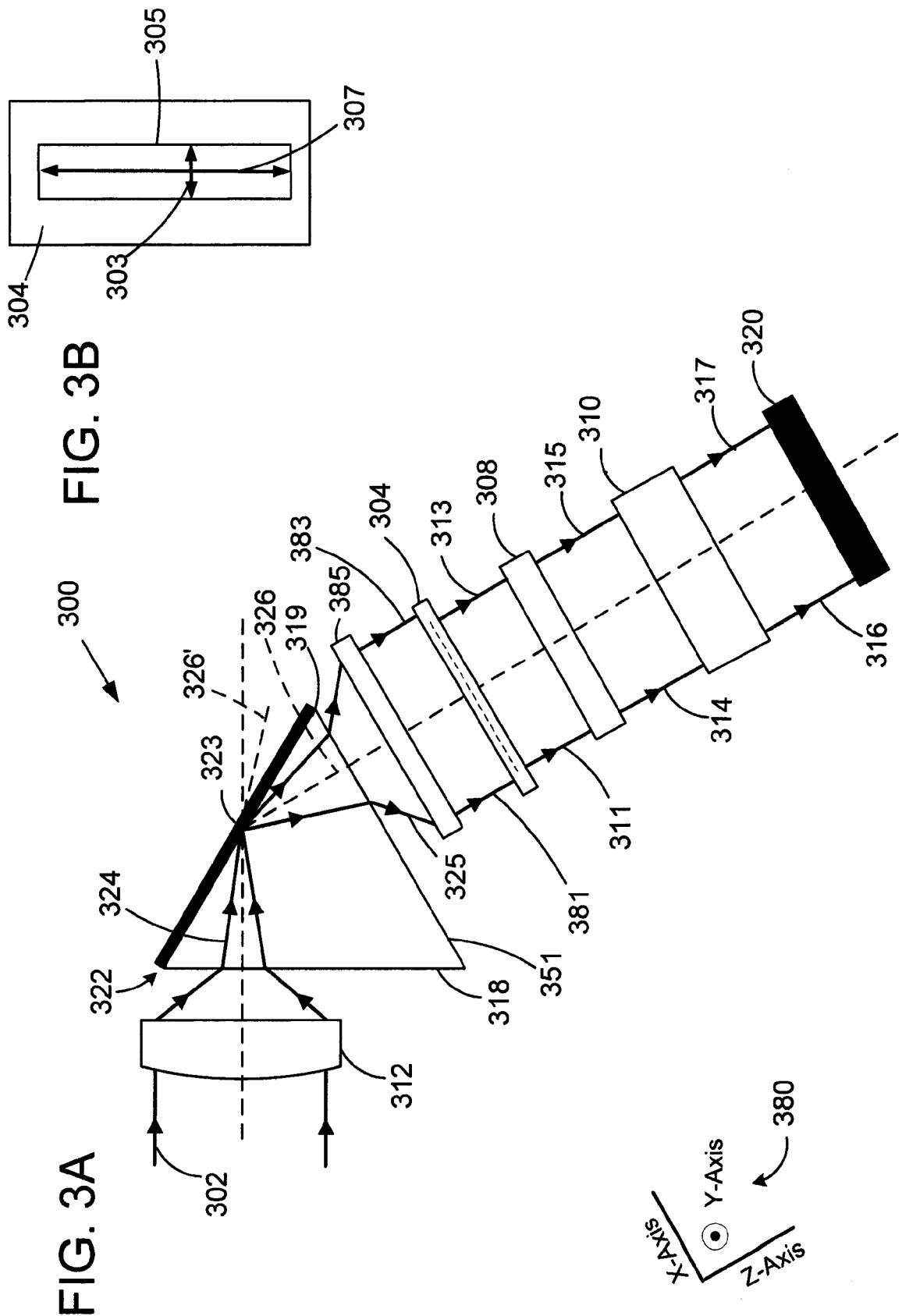
FIG. 3A is a side view of a representative critical angle refractometer in which spectral dispersion is produced after light interacts with a prism-sample interface.
Figure 4:
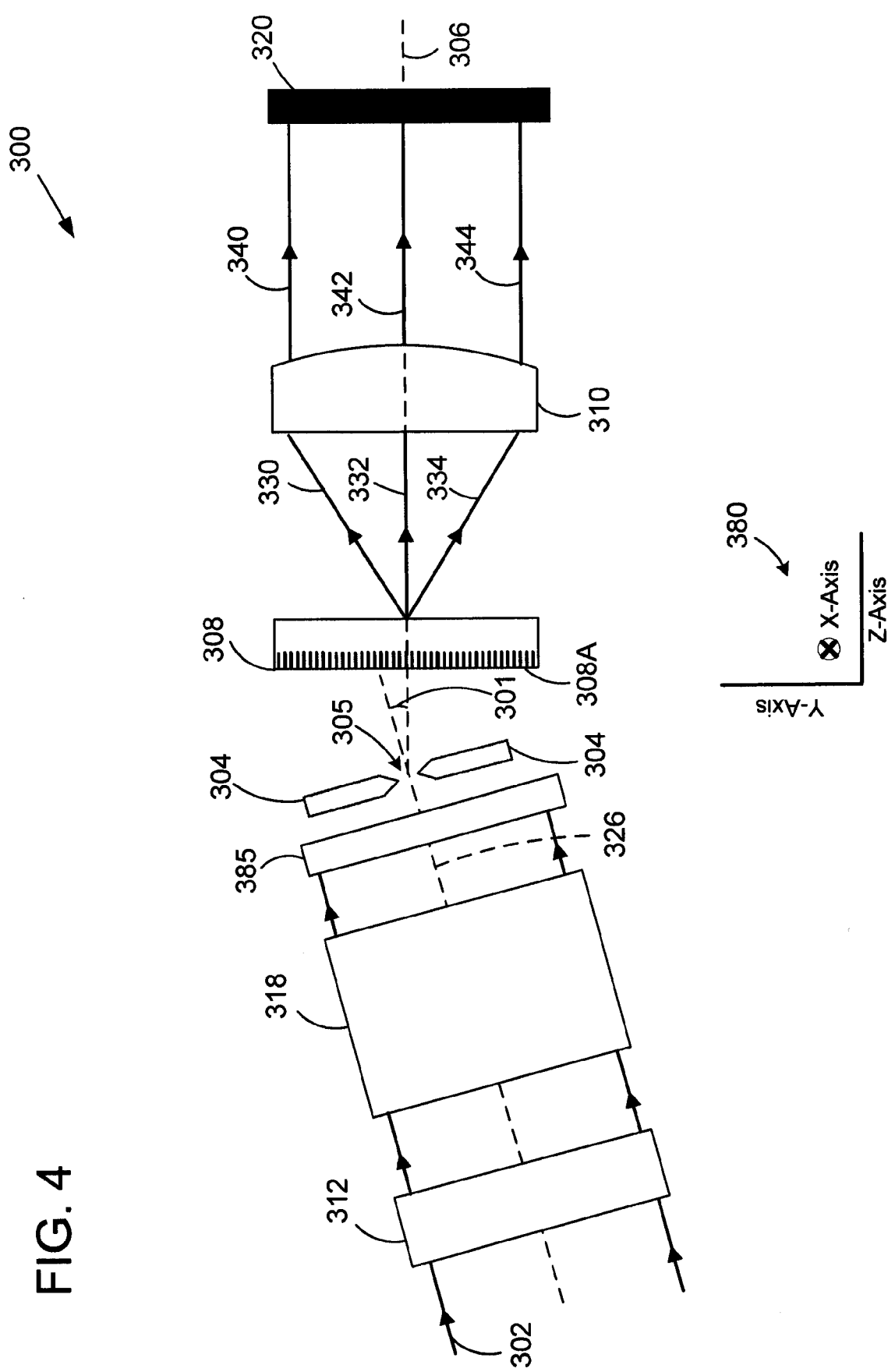
FIG. 4 is a top view of the refractometer of FIG. 3A.

FIGS. 3-4 illustrate a representative critical angle refractometer 300 in which spectral dispersion is produced after light interacts with a prism-sample interface. FIG. 3A is a side view of the refractometer 300, and FIG. 4 is a top view of the refractometer of FIG. 3A. In the following discussion, references to an xyz-coordinate system 380 are made to facilitate convenient description of the refractometer 300.

Referring to FIGS. 3A and 4, a collimated optical beam 302 is directed to a cylindrical lens 312 configured to focus the collimated optical beam on an interface 319 between a prism 318 and a sample 323. The optical beam 302 is substantially collimated in at least an xz-plane. The sample 323 is held in contact with the prism 318 using a sample holder 322. The optical beam 302 can be multi-wavelength light (e.g., generated by a broadband white light source, an infrared source, etc.), or the light can be monochromatic (e.g., generated by a discrete wavelength source or using filters). The light source (not shown) produces optical radiation that includes a range or spectrum of wavelengths over which the RI measurement is to be made.

The cylindrical lens 312 is situated to produce a focal line at the prism-sample interface 319. The cylindrical lens 312 is oriented so that the focal line is parallel to the y-axis. Focusing the light at the prism-sample interface ensures that the light is incident on the interface 319 between the prism 318 and the sample 323 at a range of angles. In order to increase the range of angles of incidence, the focal length of the cylindrical lens 312 can be decreased. Preferably, the range of angles of incidence includes the critical angle of the interface 319. For the critical angle and angles greater than the critical angle, light incident on the interface 319 between the prism 318 and the sample 323 is totally internally reflected and directed along an axis 326. For angles less than the critical angle, the optical beam is typically partially transmitted and partially reflected.

The sample 323 can take various forms (i.e., liquid, gas, liquid-gel, etc.) and can be made to contact the surface of the prism 318 using various techniques. For example, the holder 322 can be the same or substantially the same as the sample holder 122 described above with respect to FIGS. 1A and 2.

The refractive index of the prism 318 is selected based on the anticipated refractive index of the sample 323. Specifically, in order for total internal reflection to occur at the interface 319 between the sample 323 and the prism 318, the RI of the prism 318 must be higher than the RI of the sample 323. Because the RI of the prism 318 theoretically defines the maximum RI that can be measured by the refractometer 300, it is generally preferred to select a prism 318 with a high RI. For example, the prism 318 can be made of SF10 optical glass or sapphire when the range of wavelengths includes the visible spectrum. The prism 318 can be made of silicon or germanium when RI measurements are made using infrared wavelength sources. However, other materials can also be used. In addition, choosing a prism 318 with a high RI can improve wavelength resolution for long wavelengths where dispersion effects of the prism compromise TIR resolvability.

Although the prism 318 is illustrated as a single equilateral prism, other types of prisms or multiple prisms can be used. For example, a right angle prism such as a 30-60-90 prism can be used. Various other suitable prism configurations can be used, such as those described in further detail below. It may be desirable to select a prism shape so as to avoid TIR of light at the prism-air interface at other prism surfaces. In some examples, the prism is a glass block or slab or a dielectric substrate that does not have a triangular-shaped geometry.

Referring to FIG. 3A, the optical beam produced by the cylindrical lens 312 is refracted, as shown by ray line 324, upon entering the prism 318. Light reflected off of the prism-sample interface 319 is directed along the axis 326 to a collimating lens system 385. The collimating lens system produces an optical beam that is collimated at least in the yz-plane as shown by ray lines 381, 383.

The collimated optical beam produced by the collimating lens system 385 is directed to an aperture plate 304 that defines a slit 305, which produces an optical beam associated with outermost ray lines 311, 313 in the xz-plane. FIG. 3B is a front enlarged view of the aperture plate 304 and illustrates the dimensions of the slit 305. As shown in FIG. 3B, the slit 305 has a shorter dimension 303 (width W) and a longer dimension 307 (length L) perpendicular to the shorter dimension in a plane defined by the aperture plate 304. The aperture plate 304 is situated within the refractometer 300 so that the longer dimension 307 is parallel to the x-axis.

In general, the dimensions of the slit 305 are selected in association with the angular spread of the optical beam from the collimating lens to minimize or reduce spectral overlap. Typically, the optical beam is substantially collimated and the slit width W is selected so as to reduce or eliminate spectral overlap in the diffracted optical beam produced by the diffraction grating 308. For example, the slit 305 can reduce the angular spread of the optical beam in the yz-plane to improve collimation. Wide slits are associated with greater spectral overlap and reduced spectral resolution, but do permit higher power in the diffracted optical beam.

Because the slit 305 can reduce the intensity of the optical beam received from the refractometer thereby reducing signal-to-noise ratio, it is generally preferred to select a relatively large slit width W. For example, the slit width W can be 10, 100, 200, 500 or 1000 times a central wavelength or other wavelength associated with the optical beam 381, 383. The slit length L is typically much larger than the width W and is selected based on the preferred size of the optical beam in the xz-plane. For example, the length L can be approximately the same size or greater than the aperture of the cylindrical lens 310 in the xz-plane. In some implementations, the slit 305 may not be needed. For example, spectral resolution of the refractometer 300 may be sufficient without use of the slit 305.

Referring further to FIG. 3A, the optical beam is received from the slit 305 by a diffraction grating 308. The grating 308 is situated so as to produce a spectrally dispersed beam that remains collimated within the xz-plane, as illustrated by ray lines 314, 315. Referring to FIG. 4, a groove layer 308A of the grating 308 includes grooves oriented parallel to the x-axis and parallel to the longer dimension 307 of the slit 305. The grating 308 diffracts the optical beam within the yz-plane, as illustrated by ray lines 330, 332, 334. The optical beam is spectrally spread by the grating 308 so that the wavelength of the spectrally dispersed optical beam varies in the yz-plane as a function of distance from (or angle of propagation relative to) an optical axis 306.

Although the grating 308 is illustrated as a transmissive grating, the refractometer 300 can be modified to instead include a reflective grating 308. In general, angular resolution of the refractometer depends at least in part on the dispersive effect of the grating 308. Thus, the grating 308 is preferably configured to produce a large dispersion. Since angular separation increases as groove or slit separation decreases, the grating can have a groove or slit spacing that is on the order of the wavelength being measured. For example, the spacing can be between about 1.5, 2, 3, 4 or 5 times the central wavelength or other wavelength associated with the optical beam 302. The grating 308 can be an enhanced resolution transmission grating, a blazed grating, a holographic grating, or other spectrally dispersive element. Additionally, any other dispersive optical component configured to separate spectral components of an optical beam such as prisms can be used.

As shown in FIG. 4, the optical beam 302 can be oriented at an angle 301 relative to the optical axis 306. The angle 301 can be selected so that the range of wavelengths at which critical angle is being measured is approximately centered on the optical axis 306. For example, ray lines 330 and 334 represent the directions of propagation associated with maximum and minimum wavelengths within the selected wavelength range. Ray line 332 represents a direction of propagation of a central wavelength within the selected wavelengths range. Ray lines 330, 332, 334 are typically associated with a first diffraction order produced by the grating 308, but other diffraction orders can be used.

The spectrally dispersed beam produced by the diffraction grating 308 is received by a cylindrical lens 310 to produce a collimated, spectrally dispersed beam as indicated by ray lines 316, 317. The cylindrical lens 310 is positioned and oriented so as to collimate the spectrally dispersed beam in the direction of the diffraction produced by the grating 308. That is, the cylindrical lens 310 collimates the spectrally spread beam in the yz-plane, and the optical beam produced by the cylindrical lens 310 is also spectrally separated. For example, as shown in FIG. 4, the cylindrical lens 310 redirects the light propagating according to ray line 330 along ray line 340, the light propagating according to ray line 332 along ray line 342, and the light propagating according to ray line 334 along ray line 344. As shown, ray lines 340, 342, 344 are substantially parallel to but spatially separated from each other at the output of the cylindrical lens 310. As shown in FIG. 3A by the ray lines 316, 317, the optical beam produced by the cylindrical lens 310 is unchanged in the xz-plane and remains collimated in the xz-plane. Typically, the grating 308 and the cylindrical lens 310 are separated by a focal length of the cylindrical lens 310 so that the spectrally dispersed beam 314, 315 is collimated in the yz-plane.

The aperture of the cylindrical lens 310 can be selected so as to sufficiently collect diffracted light associated with the selected wavelength range. For example, the size and focal length of the cylindrical lens 310 can be selected so that, based on the divergence angles of the light 330, 334 and the separation between the grating 308 and the cylindrical lens 310, the range of wavelengths being measured is collected by the cylindrical lens 310 and has sufficient spatial separation.

For example, it may be desirable to have the spatial separation of the wavelengths match the size of a detector 320, e.g. so as to fill the active area of the detector 320. In some implementations, the dispersive effect of the grating 308 can be increased by increasing the focal length of the cylindrical lens 310. In this manner, the spatial separation of the wavelengths is increased, independent of the angular spread of the wavelengths.

The optical beam produced by the cylindrical lens 310 is directed to a detector 320, such as a CCD sensor or other sensor capable of detecting the selected range of wavelengths. The detector 320 can be a full-field sensor, capable of generating a two-dimensional image from the detected light intensity.

In general, the resolution of the refractometer 300 can be increased by increasing the dimensions of the collimated, spectrally dispersed optical beam received by the detector 320 (i.e., the optical beam represented by ray lines 316, 317 in the xz-plane and by ray lines 340, 342, 344 in the yz-plane). The active area of the detector 320 can also be increased correspondingly. The dimensions of the collimated, spectrally dispersed optical beam received by detector 320 depends on several factors, including the size and the focal length of the cylindrical lens 310 as well as the distance between the collimator 385 and the prism 318. For example, increasing the distance between the collimator 385 and the prism (i.e., the distance between the detector 320 and the prism 318 along the axis 326) can increase the dimensions of the collimated, spectrally dispersed optical beam 316, 317. In addition, increasing the focal length and size of the cylindrical lens 310 can increase the size of the collimated, spectrally dispersed optical beam. The refractometer 300 can be configured so that the size of the collimated, spectrally dispersed optical beam is such that the active area of the detector 320 is completely filled. In some implementations, the detector 320 may be configured to detect less than the entire range of angles of incidence. Although the detector 320 is illustrated as receiving light reflected at the interface 319 of the prism 318 and the sample 323, the refractometer 300 can be re-configured so that the detector 320 receives transmitted light. For example, the detector 320 can be positioned along the side of the prism 318 with the sample 323 and positioned in the path of refracted, transmitted light along the axis 326'.

Refractometers such as those illustrated in FIGS. 1-4 can also include polarizers and filters. For example, the refractometers can be configured so that the prism-sample interface is illuminated with polarized light and the light received by the detector is polarization filtered, where the polarization of the collected light is the same as that of the illumination light. Such a configuration may be useful for reducing detection of light scattered off the sample and/or prism-sample interface and can improve the resolution of the RI measurement. For example, by selecting a p-polarization for an optical beam, contrast between reflected and totally internally reflected angles can be enhanced.

Refractometers such as those illustrated in FIGS. 1-4 can be used for hyperspectral and/or real-time measurement of RI dispersion (i.e., the wavelength dependency of the RI). For example, the RI dispersion of a sample can be determined from a single refractometer image. In some examples, more than one image can be collected and used to determine RI. For example, signal to noise ratio can be improved by averaging images or by time-integrating each image. This can be referred to as instantaneous or nearly instantaneous RI measurement. Images can be collected in real-time or time integrated over a short time frame to generate real-time (or nearly real-time) video. In this manner, changes in RI dispersion can be detected as a function of time. This can be useful for the observation of chemical reactions or other time-dependent processes. Multi-wavelength RI measurement is enabled when the RI for more than one wavelength is calculated from an image. This can also be referred to as simultaneous measurement of RI over a range or plurality of wavelengths.

The measured dispersion profile can be continuous or discrete over a range of wavelengths, depending on the light source of the refractometer. That is, the measurement can be hyperspectral based on the light source and the range of wavelengths the refractometer is configured to detect. In addition, the RI measurement can be made over a range of wavelengths without scanning, rotating or other mechanized motion of optical components (e.g., neither the prism nor the sample needs to be rotated.)

The refractometers described herein can be configured to measure RI for ranges of wavelengths including but not limited to the visible spectrum. For example, the refractometers can be modified to measure RI over a range of infrared wavelengths. In this case, the optical components of the refractometer can be selected based on performance in the selected range of wavelengths.

Because RI is sensitive to temperature, the refractometers described herein can include temperature compensation. For example, a temperature correction factor can be calculated or otherwise determined for one or more of the optical components of the refractometer. Such a correction factor would represent the temperature sensitivity of the component over a range of temperatures. The correction factor could be incorporated into the RI calculations based on the temperature of the refractometer when the measurement was made. Alternatively, a refractometer can be situated in a temperature controlled environment.

The refractometers described herein, such as those illustrated in FIGS. 1-4, produce two-dimensional (2D) images with light intensity values that vary as a function of wavelength along a first axis and as a function of angle of incidence along a second axis. Therefore, wavelength and angle of incidence can be independently detected. For example, the first axis can be the y-axis and the second axis can be the x-axis. However, the first and the second axes need not be perpendicular. The pixels of the image can be mapped or calibrated to the range of wavelengths and range of angles of incidence detected. For example, each pixel y-value can be correlated with a wavelength value and each pixel x-value can be correlated with an angle of incidence value. Critical pixels can be determined for each wavelength value by identifying a position along the second axis (e.g., x-values) corresponding to the critical angle. Because refractive index can be determined from the critical angle using Snell's law, as discussed above, refractive index as a function of wavelength (e.g., dispersion) can be calculated using the identified critical pixels. By calculating the wavelength dependent RI for samples with known dispersion relationships, the refractometer can be calibrated for use with samples having unknown RI profiles.

Figure 5:
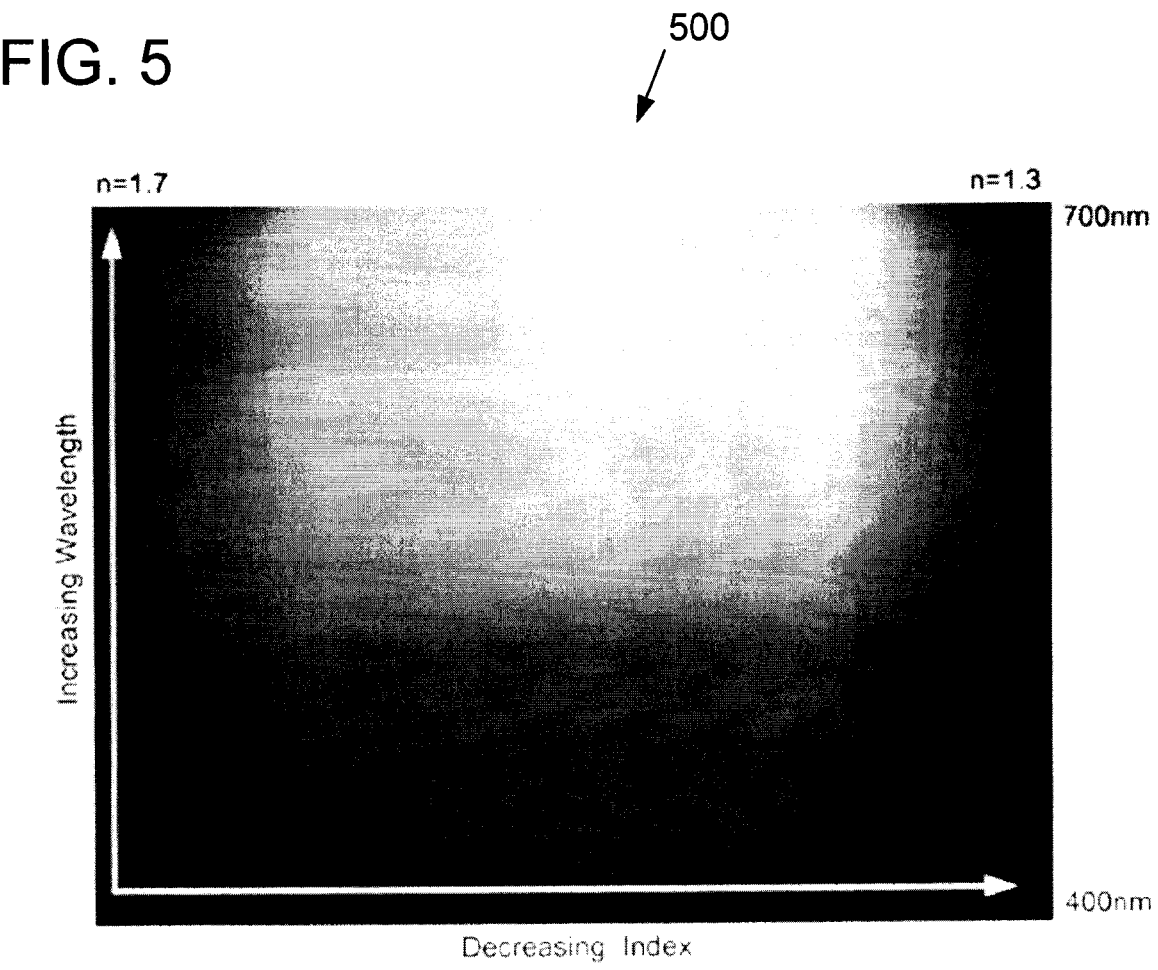
FIG. 5 is a representative image produced by a refractometer with no sample.

FIG. 5 is a representative image 500 produced by a refractometer with no sample (i.e., air is the sample). The image 500 has been mapped to a representative range of wavelengths measured by the refractometer (400 nm to 700 nm) and to a representative range of RI measured by the refractometer (1.3 to 1.7). What follows is a discussion of an exemplary calibration procedure. The calibration procedure can be used to estimate RI from images generated by refractomers such as those illustrated in FIGS. 1-4.

In general, calibration involves two parts: (1) wavelength calibration (i.e., the correlation of pixel y-values to wavelength) and (2) refractive index calibration (i.e., the correlation of pixel x-values and y-values to refractive index).

Wavelength calibration can be accomplished using refractometer images generated with no sample (i.e., air is the sample) and one or more input light sources with known spectral intensities across the range of wavelengths at which RI is to be measured. For example, when calibrating a spectrometer to measure RI over the range of wavelengths from 400 nm to 700 nm, the wavelength calibration can be performed using two gas discharge lamps, such as Ne and Hg(Ar) lamps, as input light sources. One or more images are collected for each light source, and a composite image can be used for the wavelength calibration.

Each column of a collected image (i.e., the y-values for each x-value) corresponds to an emission spectrum for the input light sources. For example, a plot of pixel intensity versus pixel row number (i.e., y-value) corresponds to an emission spectrum. Each peak in such an emission spectrum can be associated with a wavelength value based on the known emission spectrum for the input light source(s), thereby mapping pixel row number (i.e., y-value) to a range of wavelength values. Several columns can be selected and the row number (i.e., y-values) for each emission peak can be averaged. The averaged values can be used to derive a linear relationship (e.g., $\lambda(y)=a \cdot y+b$) between pixel row number (i.e., y-value) and wavelength ($\lambda$). (A relationship other than linear can be used, depending on the type of dispersion imposed by the grating or other dispersive component used in the refractometer.)

The wavelength resolution $R_s$ of the refractometer can be represented as follows:

$$R_s = D \cdot R_p$$

where D is dispersion (nm/pixel) and $R_p$ is pixel resolution. The dispersion D can be determined from the emission spectra or the derived $\lambda(y)$ relationship discussed above. Pixel resolution is determined by rotating the light source incidence angle on the grating (see, for example, angle 130 in FIG. 2) so that zero-order diffracted light from the grating is detected by the CCD. The full-width at half maximum (FWHM) of this detected band of light is the pixel resolution $R_p$.

The wavelength resolution $R_s$ depends on several factors, such as the detector and diffraction grating selected for use in the refractometer. For example, resolution can be improved by selecting a detector with low defects and high resolution, or large numbers of pixels and fine pixel spacing. CCD cooling and high bit data resolution may also improve wavelength resolution of the refractometer. In addition, resolution may be improved by increasing the dispersion of the grating. Wavelength calibration may not be necessary if the detector is capable of detecting wavelength with sufficient resolution.

Refractive index calibration can be performed using refractometer images generated from known samples by illuminating the prism-sample interface with an optical beam that includes the range of wavelengths over which RI is to be measured. Typically, several samples are measured with known refractive index values that extend through the range of values of interest. For example, for a refractometer to measure RI values between 1.3 and 1.7, samples having a range of RI values between 1.3 and 1.7 can be selected.

Figure 6:
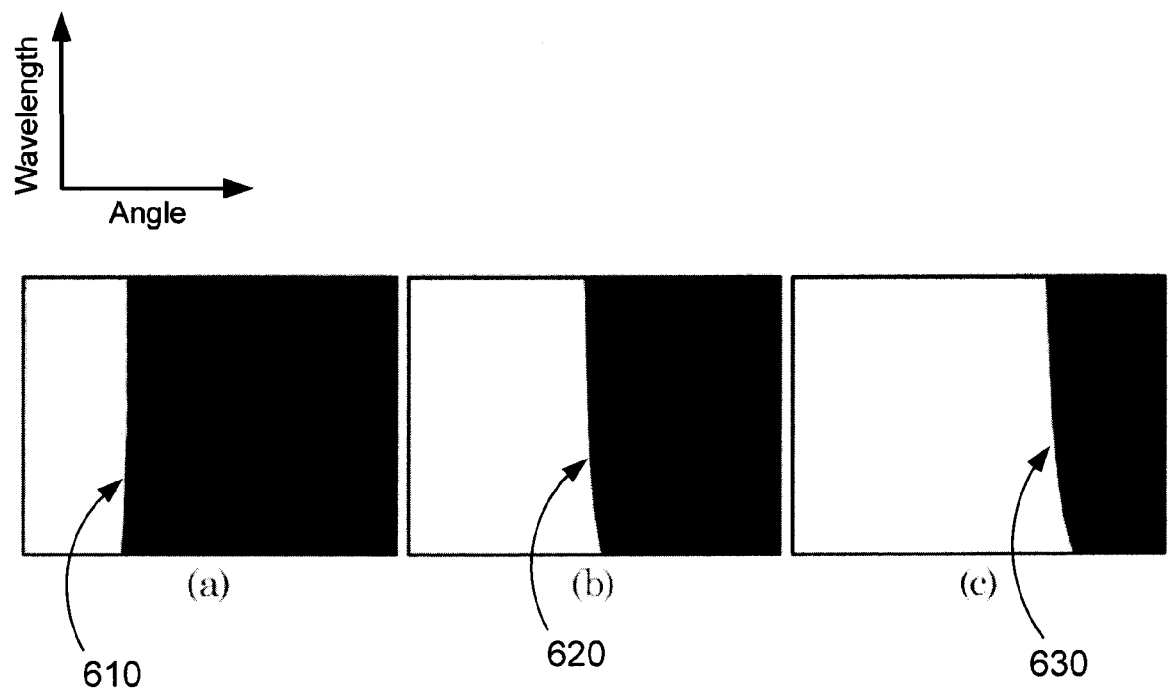
FIGS. 6A-6C illustrates representative images of samples with three different refractive index profiles.

FIG. 6 illustrates three exemplary images for three different samples generated by a refractometer detecting reflected light off of the prism-sample interface. Light is incident on the prism-sample interface at a range of angles of incidence. This range of angles corresponds to the horizontal or x-axis of each image, such that each x-value corresponds to an angle of incidence. The images have been converted to binary to facilitate visualization of the critical angle. In the images, the white region (left side) corresponds to TIR and to angles of incidence greater than the critical angle. The dark region (right side) corresponds to the absence of TIR and to angles of incidence less than the critical angle. This light is mostly transmitted and only partially reflected by the interface between the sample and the prism. The boundary between the TIR region and the partial transmission region is indicated by numerals 610, 620, 630.

The pixels that define the boundary between the light and dark region are referred to as critical pixels, and the x-values for the critical pixels correspond to the critical angles of the sample. As shown in FIG. 6 and by 610, 620, 630, critical pixel location is a function of both x and y, demonstrating that critical angle (and therefore RI) varies as a function of wavelength. This dispersion relationship can be used to identify an unknown sample.

Critical pixel locations can be obtained by identifying the pixels corresponding to the transition between partial transmission and TIR that occurs at the critical angle of incidence at the prism-sample interface. For example, techniques for extracting boundaries within an image can be used. Refractometer images can be averaged and converted to binary images, as shown in FIG. 6. Critical pixel location can also be determined using a derivative and/or a Hilbert transform. Savitzky-Golay or other image filtering techniques can be used.

Using the extracted critical pixel locations and the known dispersion profile for each sample, refractive index can be expressed as a two-dimensional function of critical pixel location (x, y). For example, the measured dispersion profiles can be represented by Cauchy coefficients, and the derived refractive index function n(x,y) can be quadratic in both x and y. The derived function n(x,y) effectively maps the two dimensional refractometer image to RI for any given x and y-values, where x and y represent the location of detected critical pixels (i.e., critical pixel locations for a test sample image). Consequently, for test samples, RI as a function of wavelength is determined from critical pixel locations in the refractometer images.

Figure 7:
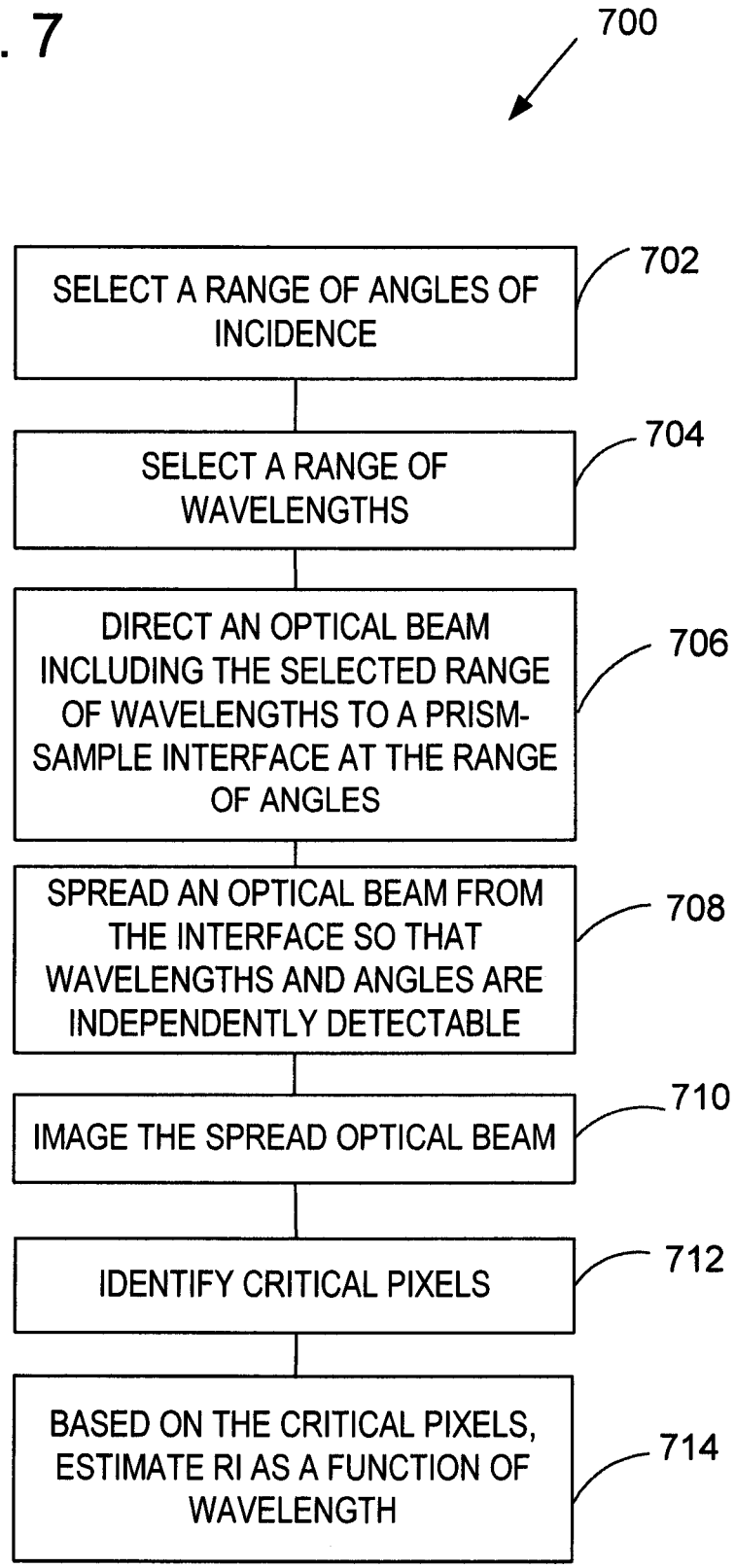
FIG. 7 is a representative method of multi-wavelength measurement of refractive index of a sample.

FIG. 7 illustrates a representative method 700 of multi-wavelength measurement of refractive index of a sample. At 702, a range of angles of incidence is selected. For example, the range of angles of incidence can be selected based on an expected range of critical angles for the sample. The range angles of incidence can be associated with a lens focal length. At 704, a range of wavelengths is selected. At 706, an optical beam that includes the selected range of wavelengths is directed to a prism-sample interface at the range of angles of incidence. For example, the directing of the optical beam can include focusing the optical beam at the interface thereby generating the range of angles of incidence at the interface. The range of angles of incidence can include a critical angle for the sample.

At 708, an optical beam from the interface is spread so that the range of wavelengths and angles are independently detectable. For example, the optical beam can be light reflected from the interface. The spreading of the light can include spectrally dispersing or spreading the light along a first axis, and the directing of the light can include focusing of the light along a second axis. The first and the second axes can be perpendicular. At 710, the spread light is imaged. For example, an imaging detector can receive the spread light and produce an image. At 712, critical pixels are identified. For example, image pixels corresponding to a transition between TIR and partial transmission can be identified. At 714, RI is estimated as a function of wavelength based on the identified critical pixels.

The method 700 need not be performed in the order illustrated in FIG. 7. For example, the spreading of the light at 708 can be performed before the directing of the selected range of wavelengths at 706. That is, at 706, an optical beam including the selected range of wavelengths is spread. At 708, the spread optical beam is directed to a prism-sample interface at the range of angles. For example, the spread optical beam can be focused on the interface. The spreading and directing of the optical beam are such that wavelengths and angles of incidence are independently detectable.

Figure 8:
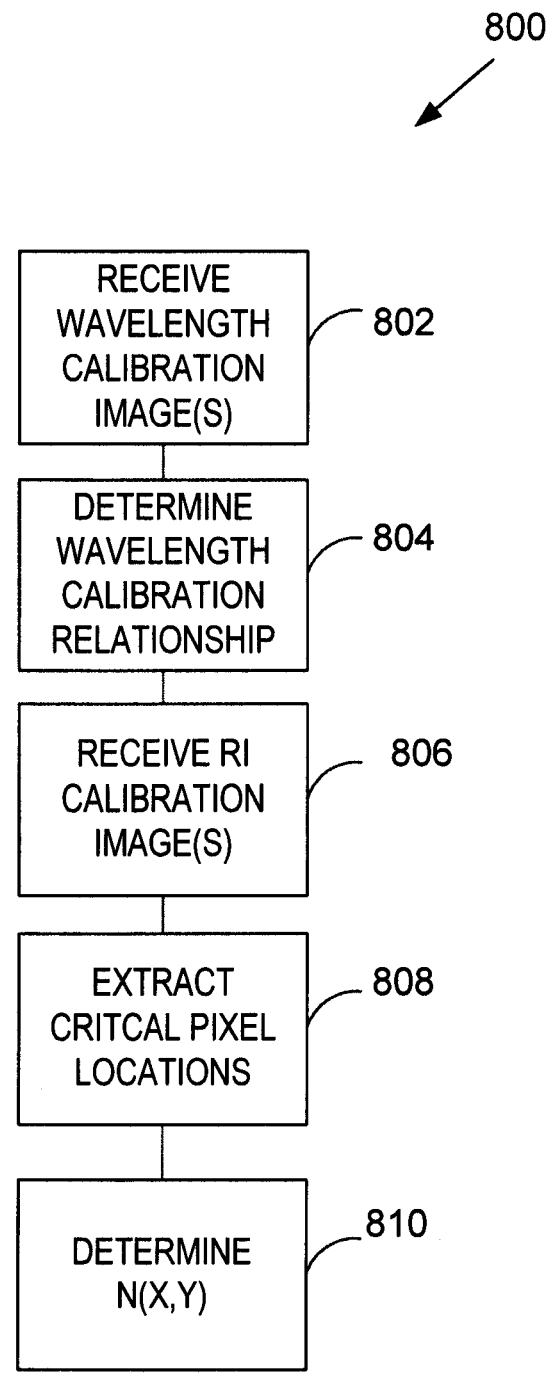
FIG. 8 is a representative method of refractometer calibration.

FIG. 8 illustrates a representative method 800 of refractometer calibration. At 802, wavelength calibration image(s) are received. For example, wavelength calibration images can include one or more two-dimensional images collected using a refractometer with no sample and with one or more light sources having known emission spectra. At 804, a wavelength-calibration relationship is determined. For example, the wavelength-calibration relationship can be an equation expressing wavelength as a function of one or more pixel coordinates. The wavelength-calibration relationship can be based on the known emission spectra and the wavelength calibration images.

At 806, refractive index (RI) calibration image(s) are received. For example, RI calibration images can include one or more two-dimensional images collected using the refractometer with one or more calibration samples having known refractive index dispersion profiles. At 808, critical pixel locations are extracted from the RI calibration image(s). At 810, refractive index as a function of critical pixel location, or n(x,y), is determined. For example, n(x,y) can be derived based on the known refractive index dispersion profiles of the one or more calibration samples.

Example Implementation

In a specific embodiment of the refractometer 100 of FIGS. 1A and 2, a quartz halogen fiber-optic light source produced a beam of collimated white light 102 that was received by the refractometer 100. The optical beam 102 included a range of wavelengths from about 400 nm to about 700 nm. The slit 104 had a width W of 150 µm and was oriented with a long dimension 107 parallel to the grooves of a transmissive diffraction grating 108. The diffraction grating 108 had a groove spacing of 830 grooves/mm. The optical beam 102 was incident on the grating 108 at an angle 101 of 27 degrees relative to the optical axis 106. At this orientation, the grating 108 produced a diffraction pattern with 550 nm light directed along (and substantially parallel to) the optical axis 106, along the ray line 132 and with 700 nm light and 400 nm light directed at approximately ±7.15 degrees from the optical axis 106 along respective ray lines 130, 134.

The spectrally dispersed optical beam produced by the grating 108 was received by a 55 mm×25 mm cylindrical lens 110 with a focal length of 150 mm at a wavelength of 589.3 nm. The cylindrical lens 110 produced a collimated, spectrally dispersed optical beam that was spectrally spread in the yz-plane. That is, light having a wavelength of 400 nm (i.e., propagating along ray line 144) and light having a wavelength of 700 nm (i.e., propagating along ray line 140) were separated by about 37 mm. The distance between the cylindrical lens 110 and the grating 108 was approximately equal to the focal length of the cylindrical lens 110. The collimated, spectrally dispersed optical beam was then received by a 25 mm×50 mm cylindrical lens 112 having focal length of 25 mm at a wavelength of 589.3 nm.

The cylindrical lens 112 focused the collimated, spectrally dispersed beam onto the prism-sample interface of a 60 mm equilateral dispersing prism 118 made of SF10 with a RI at 589 nm of 1.7667. The sample 123 was held in contact with the prism 118 using a sample holder 122. The light reflected off the prism-sample interface was received by a non-cooled monochrome 39 megapixel full frame CCD. The captured images were digitized at 12-bit resolution by a timing board and transferred to a computer for processing using a frame grabber. The generated images included 5502 rows and 7344 columns of pixels.

Wavelength calibration was performed using Ne and Hg(Ar) gas discharge lamp as the input light sources and with air as the sample. The images were generated serially with the two sources. Eight different columns of the composite image were selected as emission spectra to be used for the calibration, and seven emission spectrum peaks were selected from each spectra. The wavelength values for each peak were averaged across the selected spectra, and the relationship between pixel row number (i.e., y-value) and wavelength ($\lambda$) was calculated as follows:

$$\lambda(y) = -0.0554y + 688.13.$$

The average standard deviation for the seven peaks was 7.5 pixels. The spectral emission lines were approximately 100 pixels wide (i.e., the full-with half max (FWHM) value) for Hg(Ar). The dispersion D was 0.056 nm/pixel, and the pixel resolution was determined to be 144 pixels. Thus, the refractometer resolution was calculated to be 6.38 nm.

Refractive index calibration was performed using 11 different samples with known RI dispersion profiles. The samples were characterized by the following RIs: n=1.32, 1.35, 1.38, 1.41, 1.44, 1.48, 1.52, 1.56, 1.59, 1.62, and 1.65. For each of these samples, the Cauchy coefficients were known. Images were acquired for each sample with a three second integration time. Critical pixels were extracted using the Hilbert transform and Savitzky-Golay filtering. Using the known Cauchy equation for each sample and the extracted critical pixel locations, the following empirical relationship was derived for refractive index:

$$n(x,y) = 1.7474 - 3.5108 \times 10^{-5} x - 7.0094 \times 10^{-7} y - 4.2454 \times 10^{-9} x^2 + 1.7019 \times 10^{-9} y^2.$$

where x and y correspond to critical pixel location.

Subsequently, the RI of a validation or test sample was determined using three consecutive refractometer measurements and the RI relationship n(x,y) shown above. The images were collected and critical pixel locations were extracted from the images using techniques described above for the known samples. The table below provides a comparison of the actual RI value for the validation sample, as determined from manufacturer-provided Cauchy coefficients, to experimental RI values.

| $\lambda$(nm) | Exp. RI | Cauchy RI | Difference | % Diff. |
|---|---|---|---|---|
| 450 | 1.51260 | 1.51329 | −0.00069 | 0.05 |
| 500 | 1.50647 | 1.50709 | −0.00062 | 0.04 |
| 550 | 1.50102 | 1.50265 | −0.00163 | 0.11 |
| 600 | 1.49762 | 1.49937 | −0.00175 | 0.12 |
| 650 | 1.49610 | 1.49686 | −0.00077 | 0.05 |

The maximum difference between the validation sample data and the actual RI computed from the Cauchy coefficients occurred at 414 nm and was 0.0036 units (0.24% of the actual RI). The variation between the three measurements was negligible (i.e., below the refractometer RI resolution), with an average standard deviation of 0.000132 and a maximum of 0.000743. The three second integration time used provided for an average image contrast ratio (CR) of 0.88 at about 90% max light source output, where CR=(max−min)/(max+min) intensities. In comparison, CR was 0.01 for three milliseconds integration time.

The resolution of this refractometer system could be increased by using a zero-defect scientific-grade sensor, instead of an engineering-grade CCD sensor, and implementing CCD cooling. Additionally, the pixel data resolution of the evaluation electronics could be increased from 12-bits to 32-bits or higher. Furthermore, using a prism with a greater RI could improve resolution at longer wavelengths, where dispersion effects reduce the prism RI and therefore the TIR resolvability of the system. The use of a more intense light source could improve signal to noise ratio so that integration time could be reduced to durations more suitable for video frame rate (i.e., real-time or nearly real-time) RI measurement.

Example Multi-Reflection Configurations

FIGS. 9-14 illustrate exemplary prism configurations which can be used in place of prism 118 in refractometer 100, in place of prism 318 in refractometer 300, or in other refractometers. In the prism configurations illustrated in FIGS. 9-14, any illustrated prism can comprise a single integral prism or an assembly comprising one or more sub-prisms so that critical angle reflectance occurs at more than one sample-prism interface. If a common sub-prism material is used to define multiple interfaces, a beam angle of incidence is generally arranged to be the same (or nearly so) at all such interfaces. If different materials are used, beam angles of incidence can be arranged so that a product of sub-prism refractive index and angle of incidence is constant (or nearly so) across the interfaces.

The configurations illustrated in FIGS. 9-14 include plural samples. In any of the illustrated embodiments, the samples can comprise the same material(s) as one another, in which case they can be thought of as a single sample to be investigated. The plural samples of the illustrated embodiments can be distributed at one or more surfaces and/or one or more surface areas of the respective prisms.

As used herein, a prism is one or more dielectric solids formed of a material that is transmissive to optical beams in a particular spectral region of interest. Representative materials suitable for use in prisms include SF10 optical glass, sapphire, silicon, or germanium, as described above. Prisms generally are defined by one or more planar surfaces that are situated to couple optical beams into the prism and so that input optical beams are incident to at least one surface at a range of angles of incidence. In some examples, one or more surfaces can be provided with a reflective coating such as a metallic layer, or a multi-layer dielectric coating. Prisms can have two or more or no parallel surfaces, and can have square, rectangular, triangular, rhomboidal, parallelogram, trapezoidal, or other cross-sectional shapes. In some cases, prisms can have curved surfaces.

Figure 9:
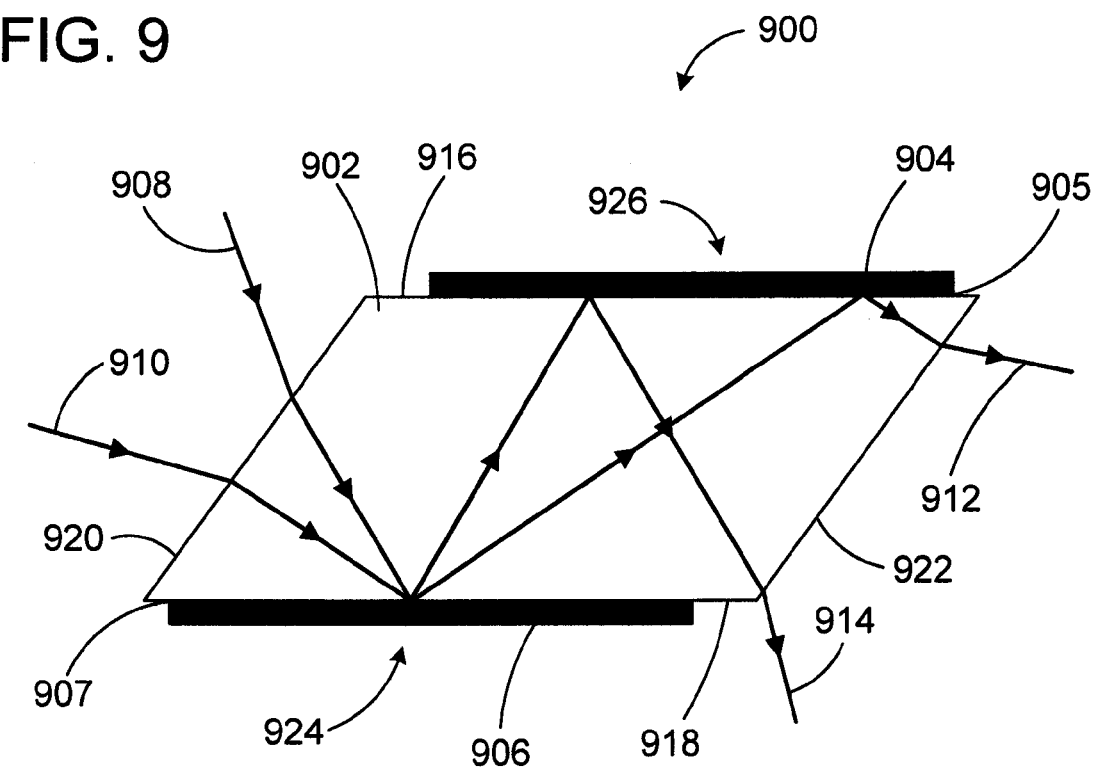
FIG. 9 is a side view of a system including a prism having a cross-sectional shape comprising a parallelogram.

FIG. 9 illustrates an exemplary system 900 including exemplary prism 902 having a cross-section corresponding to a parallelogram and having a first set of parallel surfaces 916, 918, and a second set of parallel surfaces 920, 922. A sample 904 can be in contact with surface 916 of the prism 902, and a sample 906 can be in contact with the surface 918 of the prism 902. The samples 904, 906 can be situated such that they extend along the respective surfaces 916, 918 of the prism 902. For example, as described above, the samples 904, 906 can be held in place with a sample holder (not illustrated in FIG. 9).

An optical beam is directed by a cylindrical lens (e.g., lens 112 or lens 312) into the prism 902 as indicated by ray lines 908, 910. Upon entering the prism 902, the optical beam is refracted and continues through the prism 902 toward a prism-sample interface 907, where at least a portion of the optical beam can be reflected at a first reflection area 924 toward surface 916 of the prism 902. A reflected beam portion continues through the prism 902 toward a prism-sample interface 905, where at least a portion of the optical beam can be reflected a second time at a second reflection area 926. A portion of the optical beam reflected at the prism-sample interface 905 continues through the prism 902 toward the surface 922 of the prism 902. At surface 922, the twice-reflected optical beam portion is refracted and exits the prism 902, as indicated by ray lines 912, 914.

The refractometer system within which the system 900 is used (e.g., refractometer 100 or refractometer 300) can be configured such that the optical beam exiting the prism 902 is directed to and received by a detector (e.g., detector 120 or detector 320). In such a system, the optical beam received by the detector will have been reflected at both the prism-sample interface 905 and the prism-sample interface 907.

Figure 10:
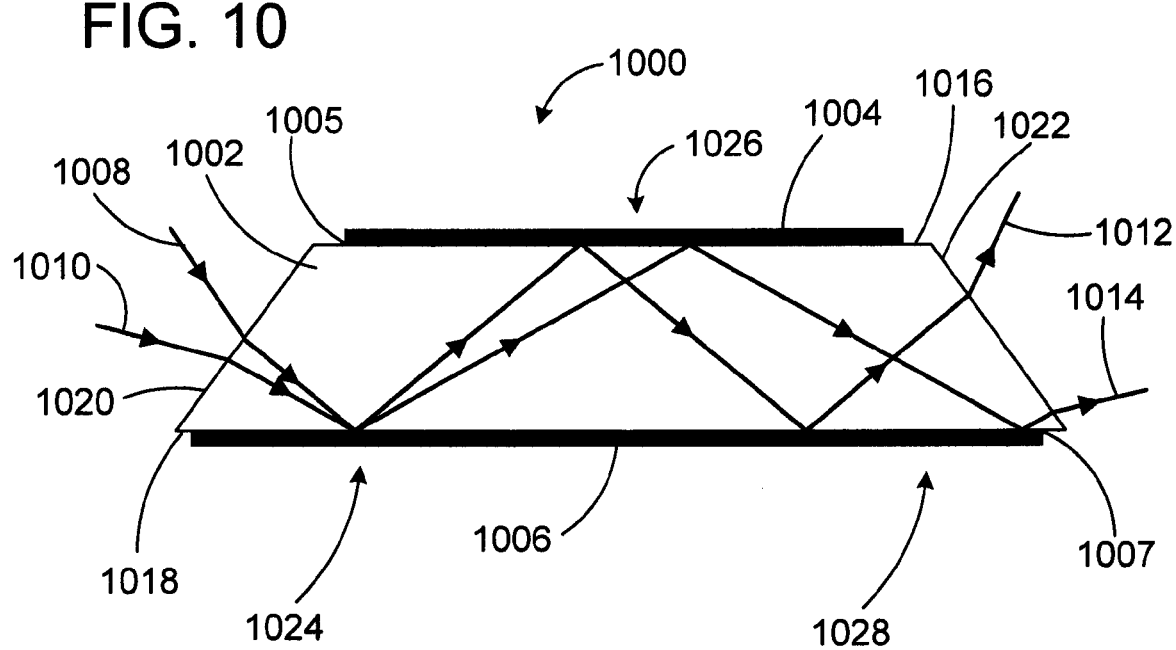
FIG. 10 is a side view of a system including a prism having a cross-sectional shape comprising a trapezoid.

FIG. 10 illustrates an exemplary system 1000 including exemplary prism 1002 having a cross-section corresponding to a trapezoid and having a first set of opposing surfaces 1016, 1018, and a second set of opposing surfaces 1020, 1022. A sample 1004 can be in contact with surface 1016 of the prism 1002, and a sample 1006 can be in contact with the surface 1018 of the prism 1002. The samples 1004, 1006 can be situated such that they extend along the respective surfaces 1016, 1018 of the prism 1002. For example, as described above, the samples 1004, 1006 can be held in place with a sample holder (not illustrated in FIG. 10).

An optical beam is directed by a cylindrical lens (e.g., lens 112 or lens 312) into the prism 1002 as indicated by ray lines 1008, 1010. Upon entering the prism 1002, the optical beam is refracted and continues through the prism 1002 toward a prism-sample interface 1007, where at least a portion of the optical beam can be reflected at a first reflection area 1024 toward surface 1016 of the prism 1002. A reflected beam portion continues through the prism 1002 toward a prism-sample interface 1005, where at least a portion of the optical beam can be reflected a second time at a second reflection area 1026. A portion of the optical beam continues from the prism-sample interface 1005 through the prism 1002 toward the prism-sample interface 1007, where at least a portion of the optical beam can be reflected a third time at a third reflection area 1028. A portion of the optical beam reflected at the prism-sample interface 1007 continues through the prism 1002 toward the surface 1022 of the prism 1002. At surface 1022, the reflected beam portion is refracted and exits the prism 1002, as indicated by ray lines 1012, 1014.

The refractometer system within which the system 1000 is used (e.g., refractometer 100 or refractometer 300) can be configured such that the optical beam exiting the prism 1002 is directed to and received by a detector (e.g., detector 120 or detector 320). In such a system, optical beam received by the detector will have been reflected at the prism-sample interface 1005 once and at the prism-sample interface 1007 twice.

Figure 11:
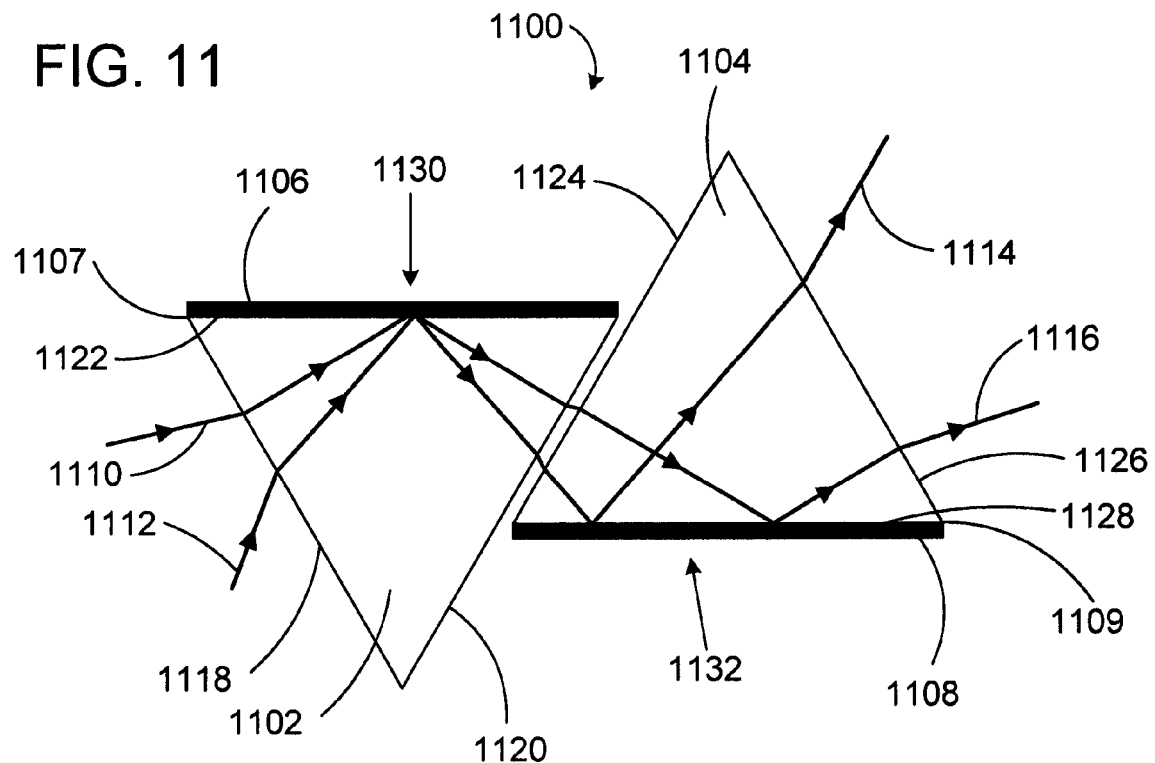
FIG. 11 is a side view of a system including two prisms having cross-sectional shapes comprising triangles.

FIG. 11 illustrates an exemplary system 1100 including exemplary first prism 1102 and exemplary second prism 1104. First prism 1102 has a cross-section corresponding to a triangle and has three surfaces 1118, 1120, and 1122. Second prism 1104 has a cross-section corresponding to a triangle and has three surfaces 1124, 1126, and 1128. In the illustrated system, first prism 1102 and second prism 1104 have shapes comprising equilateral triangles of the same dimensions, but in alternative embodiments, the two prisms 1102, 1104 can comprise other shapes (e.g., non-equilateral triangles) and need not have the same dimensions as one another. The prisms 1102, 1104 can comprise the same material as one another, or can comprise different materials, depending on the requirements of the particular system.

A sample 1106 can be in contact with surface 1122 of the prism 1102, and a sample 1108 can be in contact with the surface 1128 of the prism 1104. The samples 1106, 1108 can be situated such that they extend along the respective surfaces 1122, 1128 of the respective prisms 1102, 1104. For example, as described above, the samples 1106, 1108 can be held in place with a sample holder (not illustrated in FIG. 11).

In the illustrated system, surface 1120 of prism 1102 and surface 1124 of prism 1104 are parallel to one another, although in alternative embodiments, these surfaces need not be parallel to one another (e.g., in cases where one or both of the prisms 1102, 1104 have a non-equilateral triangular shape). In the illustrated system, the prisms 1102, 1104 are not in contact with one another and a space exists between them. In alternative embodiments, the space between the prisms 1102, 1104 can be larger or smaller, or the prisms 1102, 1104 can be in contact with one another.

An optical beam is directed by a cylindrical lens (e.g., lens 112 or lens 312) into the prism 1102 as indicated by ray lines 1110, 1112. Upon entering the prism 1102, the optical beam is refracted and continues through the prism 1102 toward a prism-sample interface 1107, where at least a portion of the optical beam can be reflected at a first reflection area 1130 toward surface 1120 of the prism 1102. A reflected beam portion continues through the prism 1102 toward surface 1120, where it is refracted upon exiting the prism 1102. Upon exiting the prism 1102, the reflected beam portion continues to propagate from prism 1102 toward prism 1104 through the space between the prisms 1102, 1104. Upon entering the prism 1104, the optical beam is refracted and continues through the prism 1104 toward a prism-sample interface 1109, where at least a portion of the optical beam can be reflected a second time at a second reflection area 1132. The reflected beam portion continues through the prism 1104 toward surface 1126 of prism 1104. At surface 1126, the reflected beam portion is refracted and exits the prism 1104, as indicated by ray lines 1114, 1116.

The refractometer system within which the system 1100 is used (e.g., refractometer 100 or refractometer 300) can be configured such that the optical beam exiting the prism 1104 is directed to and received by a detector (e.g., detector 120 or detector 320). In such a system, optical beam received by the detector will have been reflected at the prism-sample interface 1107 and at the prism-sample interface 1109.

Figure 12:
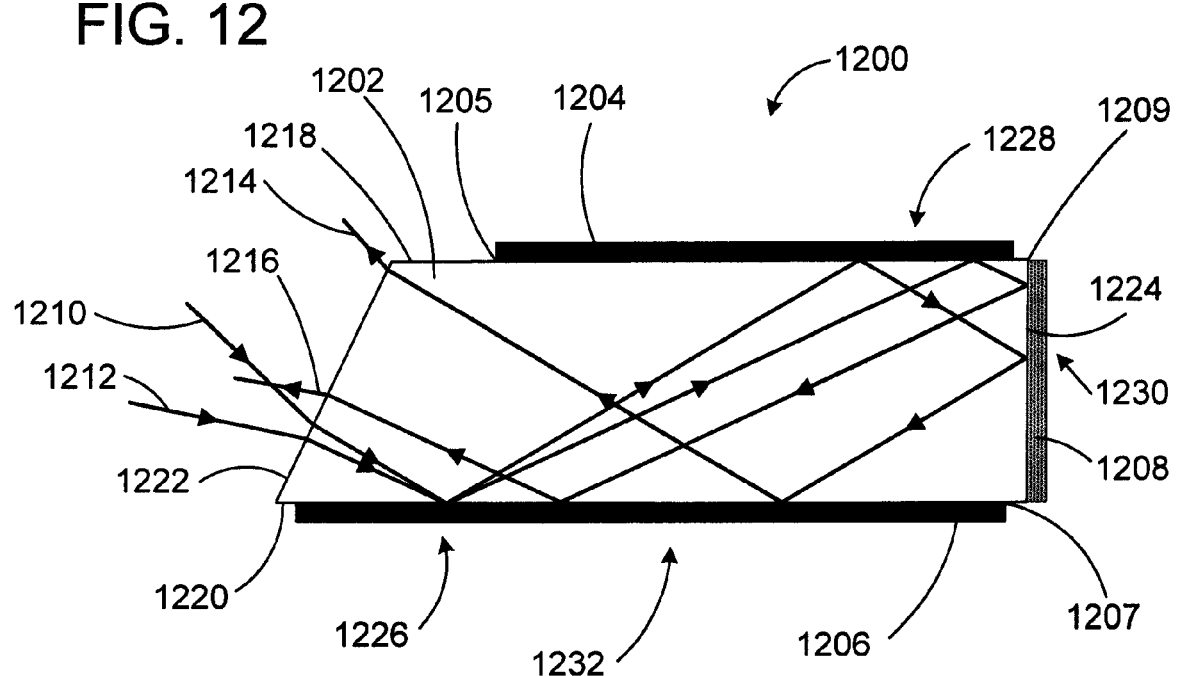
FIG. 12 is a side view of a system including a prism having a cross-sectional shape comprising a quadrilateral.

FIG. 12 illustrates an exemplary system 1200 including exemplary prism 1202 having a cross-section corresponding to a quadrilateral defined by four surfaces 1218, 1220, 1222, and 1224. A sample 1204 can be in contact with surface 1218 of the prism 1202, and a sample 1206 can be in contact with the surface 1220 of the prism 1202. The samples 1204, 1206 can be situated such that they extend along the respective surfaces 1218, 1220 of the prism 1202. For example, as described above, the samples 1204, 1206 can be held in place with a sample holder (not illustrated in FIG. 12). System 1200 can also include a reflective material 1208 in contact with the surface 1224 of the prism 1202.

An optical beam is directed by a cylindrical lens (e.g., lens 112 or lens 312) into the prism 1202 as indicated by ray lines 1210, 1212. Upon entering the prism 1202, the optical beam is refracted and continues through the prism 1202 toward a prism-sample interface 1207, where at least a portion of the optical beam can be reflected at a first reflection area 1226 toward surface 1218 of the prism 1202. A reflected beam portion continues through the prism 1202 toward a prism-sample interface 1205, where at least a portion of the reflected beam portion can be reflected a second time at a second reflection area 1228. The reflected beam portion continues from the prism-sample interface 1205 through the prism 1202 toward a prism-reflective material interface 1209, where the reflected beam portion can be reflected a third time at a third reflection area 1230. The reflected beam portion continues from the prism-reflective material interface 1209 through the prism 1202 toward the prism-sample interface 1207, where at least a portion of the reflected beam portion can be reflected a fourth time at a fourth reflection area 1232. A portion of the optical beam reflected at the prism-sample interface 1207 continues through the prism 1202 toward the surface 1222 of the prism 1202. At surface 1222, the reflected beam portion is refracted and exits the prism 1202, as indicated by ray lines 1214, 1216.

The refractometer system within which the system 1200 is used (e.g., refractometer 100 or refractometer 300) can be configured such that the optical beam exiting the prism 1202 is directed to and received by a detector (e.g., detector 120 or detector 320). In such a system, the optical beam received by the detector will have been reflected at the prism-sample interface 1205 once, at the prism-sample interface 1207 twice, and at the prism-reflective material interface 1209 once.

Figure 13:
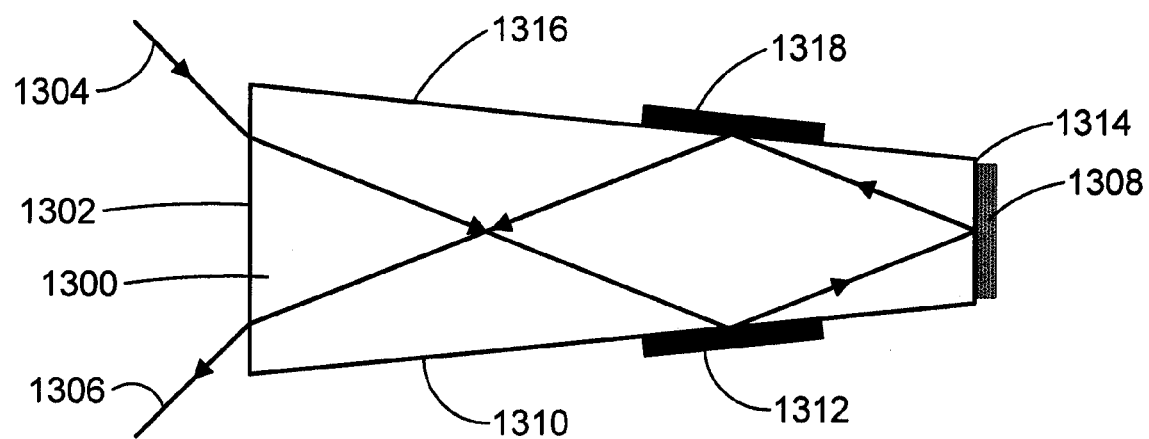
FIG. 13 is a side view of another system including a prism having a cross-sectional shape comprising a quadrilateral.

With reference to FIG. 13, a prism 1300 includes a beam coupling surface 1302 situated for coupling an optical beam into the prism 1300 along an axis 1304 and out of the prism along an axis 1306. In the example of FIG. 13, the surface 1302 is situated for beam input and output, but additional surfaces can be provided as well. An optical beam propagating along the axis 1304 is directed to a first critical angle surface 1310. Typically, the incident optical beam strikes the first critical angle surface 1310 at a range of angles of incidence that includes a critical angle, but in FIG. 13, the incident beam is represented as a single ray direction corresponding to the axis 1304 for purposes of simplicity of illustration. A first sample 1312 contacts the first critical angle surface 1310 at a surface region which receives the incident optical beam. The first critical angle surface 1310 reflects some portions of the received incident beam to prism return surface 1314 that is provided with a reflective coating 1308 such as a metallic or multilayer dielectric coating so as to direct the optical beam to a second critical angle surface 1316. A second sample 1318 contacts the second critical angle surface 1316 at a surface region which receives the optical beam from the return surface 1314. At the surfaces 1310, 1316, the optical beam is incident at range of angles that includes the critical angle defined by the sample/surface interfaces so that a beam having critical angle dependent intensity is directed out of the prism 1300 at the coupling surface 1302. Portions of the incident beam at different wavelengths are typically distributed in a direction perpendicular to the plane of FIG. 13 so that the output beam has a spectrally dependent intensity distribution that is a function of prism/sample critical angle.

As shown in FIG. 13, the first critical angle surface 1310 and the second critical angle surface 1316 are not parallel. The return surface 1314 is arranged so that beam portions that are incident to the first critical angle surface 1310 at a particular angle of incidence are incident to the second critical angle surface 1316 at the same angle of incidence, within at least 0.01, 0.1, 0.5, or 1 degree.

FIG. 13 illustrates that samples 1312 and 1318 need not be in contact with the entirety of the respective surfaces 1310, 1316 of the prism 1300. In fact, the samples 1312, 1318 can contact a relatively small portion of the respective surfaces 1310, 1316 if they contact at least the portion of the surfaces corresponding to the areas where the optical beam is to be reflected. The total amount of sample material required can depend on the total surface area of the prism where reflections occur, which can depend in turn on the degree to which the optical beam is angularly dispersed.

Figure 14:
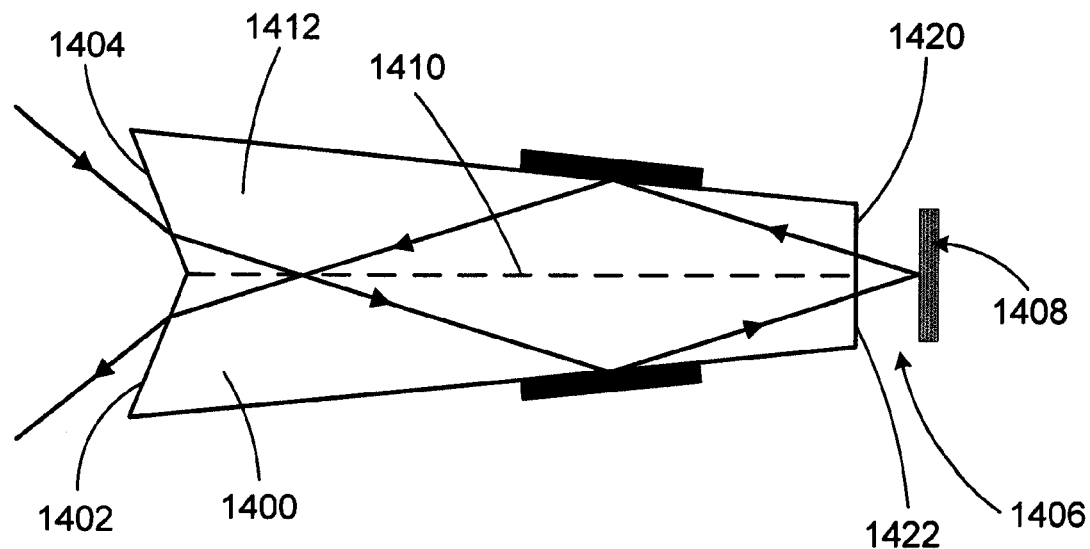
FIG. 14 is a side view of a system including a prism comprising two subprisms.

FIG. 14 illustrates an optical system similar to that shown in FIG. 13, and comprising two subprisms 1400, 1412, in contact with one another at an interface 1410, indicated by a dashed line. The prism 1412 can include a beam entrance surface 1404 and the prism 1400 can include a beam exit surface 1402, which need not be parallel to one another. As also shown in FIG. 14, a reflector 1408 need not be in contact with the prisms 1400, 1412, and the reflector 1408 and the prisms 1400, 1412 are separated by a gap 1406. Beam refraction at prism surfaces 1420, 1422 is not shown.

The systems illustrated in FIGS. 9-14 can be incorporated into refractometer systems such as refractometer 100 or refractometer 300. Thus, the optical beam propagating through any one of these systems can be spectrally dispersed prior to entering the system or after exiting the system to allow simultaneous measurement of refractive index of a material for a plurality of wavelengths of electromagnetic radiation. In the systems of FIGS. 9-14, a propagating optical beam reflects off prism-sample interfaces more than once, which can provide distinct advantages.

As explained above, FIGS. 6A-6C illustrate three exemplary images for three different samples generated by a refractometer detecting an optical beam reflected off of a prism-sample interface. The images shown in FIGS. 6A-6C were converted to binary to facilitate visualization of the critical angle at the well-defined boundary between the white and black regions. Visualization of the underlying data (prior to conversion of the images to binary) reveals less well-defined boundaries than those illustrated in FIGS. 6A-6C. That is, there can be a transition region in the raw data between the white region (corresponding to TIR and angles of incidence greater than the critical angle) and the black region (corresponding to the absence of TIR and angles of incidence less than the critical angle).

The existence of the transition region can be the result of small systemic errors inherent in refractometer systems. For example, in theory, for angles of incidence greater than the critical angle, the entire optical beam is reflected at the prism-sample interface. In practice, however, less than 100% of the optical beam incident at such angles may be reflected due to various optical effects (e.g., Rayleigh scattering). The existence of the transition region can lead to inaccuracy in the determination of the location of critical pixels and thus the ultimate measurement of index of refraction of the sample. Systems such as those illustrated in FIGS. 9-14 help to reduce these inaccuracies by introducing multiple reflections off of prism-sample interfaces. That is, each additional reflection off such an interface can amplify the difference in measurements corresponding to angles of incidence greater than the critical angle and angles of incidence less than the critical angle, thereby increasing the contrast between the white and black regions prior to conversion of the data to binary. This can lead to improved accuracy and ease in determining the location of critical pixels from raw data.

While various specific embodiments are illustrated in FIGS. 9-14, the features of these illustrated embodiments can be combined, and various other features can be incorporated in other embodiments. For example, system 1100 can include a third triangular prism and a third sample. System 900 or system 1000 can include a second prism (e.g., a prism having a cross-section having a triangle, parallelogram, or trapezoid shape) and an additional sample, arranged in a manner similar to that illustrated for system 1100. The prisms illustrated in FIGS. 9-14 can have alternative shapes or sizes. For example, prisms having lengths or other dimensions larger than those illustrated can allow additional reflections off prism-sample interfaces. In some cases, a system can include a reflective material (similar to reflective material 1208) in place of a sample. For example, in system 1000, a reflective material can be used in place of sample 1004. In such an embodiment, an optical beam propagating through system 1000 still reflects off a prism-sample interface twice, though the sample is only in contact with one surface of the prism. In system 900 or 1000, a reflective surface can be positioned against surface 922 or 1022, in a manner similar to that illustrated for system 1200. In such embodiments, additional reflections can be obtained without increasing the dimensions of the prism, and the locations at which an optical beam enters and exits the system can be proximate to one another.

FIGS. 9-12 illustrate that an angularly dispersed optical beam can have a focus at the first prism-sample interface along the path of the optical beam. In any of the systems illustrated in FIGS. 9-14, however, the optical beam can have a focus at any suitable location, such as at a second prism-sample interface along the path of the optical beam, or at the last prism-sample interface along the path of the optical beam. Alternatively, an optical beam can have a focus which is within a prism, rather than at a prism-sample interface, in which case any contamination at the surface of the prism will not be re-imaged at the detector. As yet another alternative, an optical beam need not have a focus within a prism.

In any of the systems shown in FIGS. 9-14, the samples can have different sizes. For example, the samples can cover a greater or a smaller portion of the surfaces of the prism(s) than illustrated. In any of the systems shown in FIGS. 9-14, any one or more of the prisms can comprise a plurality of sub-prisms arranged to form the shape illustrated.

In any of the systems illustrated in FIGS. 9-14, the prism-sample interfaces can be curved. In any refractometer including one of the systems shown in FIGS. 9-14, one or more of the other optical elements of the refractometer (e.g., cylindrical lenses 112, 312, or collimating lens system 385) can be combined with a prism (e.g., prism 902, 1002, 1102, 1104, 1202, 1300, 1400, 1412) to form a single integral optical element. FIGS. 9-12 illustrate that an angularly dispersed optical beam can enter a prism at a surface in a configuration in which a central ray of the optical beam is generally perpendicular to the surface of the prism. As shown in FIGS. 13 and 14, however, this need not be the case.

In view of the many possible embodiments to which the principles of the disclosed technology may be applied, it should be recognized that the illustrated embodiments are only preferred examples and should not be taken as limiting the scope of the disclosure. We claim all that comes within the scope and spirit of the appended claims.

I claim:

1. A refractometer for multi-wavelength measurement of refractive index of a sample, comprising:
a focusing optical system configured to direct an optical beam that includes a range of wavelengths to be incident on an interface between the sample and a prism at a range of angles of incidence including a critical angle, wherein the focusing optical system is configured to produce a linear illumination pattern at the interface so that the wavelength of light of the linear illumination pattern varies as a function of distance along the linear illumination pattern; and
a dispersive optical system configured to spectrally spread the optical beam so that the range of wavelengths and the critical angle are independently detectable;
wherein the refractometer is configured so that at least portions of the optical beam are totally internally reflected within the prism at a first reflection area and at least portions of the optical beam are totally internally reflected within the prism at a second reflection area.

2. The refractometer of claim 1, wherein:
the prism comprises a first surface and a second surface parallel to the first surface;
the first surface and the second surface are situated so as to contact the sample; and
the first surface includes the first reflection area and the second surface includes the second reflection area.

3. The refractometer of claim 2, wherein the optical beam is directed to the first surface and the second surface at a range of angles of incidence that includes the critical angle.

4. The refractometer of claim 3, wherein the optical beam is directed so as to be incident to the first surface at least twice.

5. The refractometer of claim 4, wherein the prism further comprises a reflective surface configured to direct the optical beam from the first surface to the second surface.

6. The refractometer of claim 5, wherein the reflective surface is perpendicular to the first surface and the second surface.

7. The refractometer of claim 3, wherein a cross-section of the prism is a parallelogram.

8. The refractometer of claim 3, wherein a cross-section of the prism is a trapezoid.

9. The refractometer of claim 1, wherein:
the prism comprises a first subprism having a first surface including the first reflection area, and a second subprism having a second surface including the second reflection area; and
the optical beam is directed to the first surface and the second surface at a range of angles of incidence that includes the critical angle.

10. The refractometer of claim 9, wherein one of the first subprism and the second subprism has a triangular cross-section.

11. The refractometer of claim 10, wherein:
the first surface is parallel to the second surface; and
the first subprism is not in contact with the second subprism.

12. The refractometer of claim 1, wherein:
a cross-section of the prism is a quadrilateral;
the prism has a first surface in contact with the sample and a second surface in contact with the sample;
the refractometer further comprises a reflective material in contact with a third surface of the prism; and
the refractometer is configured to reflect the optical beam at a third reflection area and to at least partially reflect the optical beam within the prism at a fourth reflection area.

13. The refractometer of claim 12, wherein:
the first reflection area is at an interface between the first surface of the prism and the sample;
the second reflection area is at an interface between the second surface of the prism and the sample;
the third reflection area is at an interface between the third surface of the prism and the reflective material; and
the fourth reflection area is at an interface between the first surface of the prism and the sample.

14. The refractometer of claim 1, wherein the linear illumination pattern at the interface is a focal line.

15. A refractometer, comprising:
a spectrally and angularly dispersive optical system configured to receive a collimated optical beam and to spectrally disperse a range of wavelengths of the optical beam along a first axis and angularly disperse the optical beam along a second axis that is not parallel to the first axis;
a prism in contact with a sample, wherein the prism is configured so that at least a portion of an incident optical beam is reflected within the prism at an interface between the sample and a prism surface at a first reflection area and at a second reflection area and the incident optical beam generates a linear illumination pattern at the interface;
a detection system situated and configured to detect critical angles of the sample for at least two wavelengths of the range of wavelengths based on the partial reflections of the optical beam at the first and second reflection areas;
a first cylindrical lens configured to collimate the spectrally dispersed optical beam along the first axis; and
a second cylindrical lens configured to angularly disperse the collimated spectrally dispersed optical beam along a second axis that is not parallel to the first axis and to produce the linear illumination pattern at the interface, wherein the wavelength of light of the linear illumination pattern varies as a function of distance along the first axis.

16. The refractometer of claim 15, wherein the prism has a shape comprising a parallelogram.

17. The refractometer of claim 15, wherein the prism has a shape comprising a trapezoid.

18. The refractometer of claim 15, wherein:
the prism comprises a first subprism having a first surface including the first reflection area, and a second subprism having a second surface including the second reflection area; and
the optical beam is directed to the first surface and the second surface at a range of angles of incidence that includes the critical angle.

19. A method of measuring refractive index of a sample at a plurality of wavelengths, comprising:
directing an optical beam that includes optical radiation at the plurality of wavelengths so as to generate a linear illumination pattern on an interface between the sample and a prism at a plurality of angles of incidence, thereby causing at least partial reflection of the optical beam within the prism at a first reflection area and at least partial reflection of the optical beam within the prism at a second reflection area, wherein the wavelength of light of the linear illumination pattern varies as a function of distance along the linear illumination pattern; and
spectrally spreading the optical beam to determine if the plurality of angles of incidence includes a critical angle for one or more of the plurality of wavelengths.

20. The method of claim 19, wherein the prism has a shape comprising a parallelogram.

21. The method of claim 19, wherein the prism has a shape comprising a trapezoid.

* * * * *